US011452440B2

(12) United States Patent
Palanker et al.

(10) Patent No.: US 11,452,440 B2
(45) Date of Patent: Sep. 27, 2022

(54) SYSTEM AND METHOD FOR PROVIDING ANALYSIS OF VISUAL FUNCTION USING A MOBILE DEVICE WITH DISPLAY

(71) Applicant: The Board of Trustees of the Leland Stanford Junior University, Stanford, CA (US)

(72) Inventors: Daniel Palanker, Palo Alto, CA (US); Mark Blumenkranz, Los Altos Hills, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 174 days.

(21) Appl. No.: 16/920,314

(22) Filed: Jul. 2, 2020

(65) Prior Publication Data

US 2021/0153736 A1 May 27, 2021

Related U.S. Application Data

(63) Continuation of application No. 15/424,733, filed on Feb. 3, 2017, now Pat. No. 10,702,140, which is a
(Continued)

(51) Int. Cl.
*A61B 3/00* (2006.01)
*A61B 3/02* (2006.01)
(Continued)

(52) U.S. Cl.
CPC .......... *A61B 3/0025* (2013.01); *A61B 3/0033* (2013.01); *A61B 3/0041* (2013.01);
(Continued)

(58) Field of Classification Search
CPC ... A61B 3/0025; A61B 3/0033; A61B 3/0041; A61B 3/022; A61B 3/024; A61B 3/032;
(Continued)

(56) References Cited

U.S. PATENT DOCUMENTS

| 4,408,846 A | 10/1983 | Balliet |
| H293 H | 6/1987 | Task et al. |

(Continued)

FOREIGN PATENT DOCUMENTS

| JP | 2007165976 A | 6/2007 |
| KR | 1020050018732 A | 2/2005 |

(Continued)

OTHER PUBLICATIONS

Allergan, Inc.; VisionCheck (iTunes App Store); released Feb. 23, 2011; retrieved Dec. 9, 2014 from the internet (https://itunes.apple.com/us/app/visioncheck/id420911054?mt=8).
(Continued)

*Primary Examiner* — Jack Dinh

(57) ABSTRACT

A visual function evaluation is performed using a sequence of interactions with a mobile device. A patient user may perform a variety of visual tests using the mobile device. The mobile device transmits the test results to a remote server implementing analysis of the visual function results using network service. The network service receives the test results, processes the results, and provides the processed results to a healthcare provider. The processed results may include trends of the user's visual function test performance. The healthcare provider, such as a physician, may optimize and administer treatment based on the data. Early detection of changes in visual function can enable the healthcare provider to individualize treatment, helping to prevent vision loss while minimizing visits to the office, discomfort, and expense.

20 Claims, 26 Drawing Sheets

FIGURE 1A

Related U.S. Application Data continuation of application No. 15/090,080, filed on Apr. 4, 2016, now Pat. No. 9,572,484, which is a continuation of application No. 14/352,571, filed as application No. PCT/US2012/060627 on Oct. 17, 2012, now Pat. No. 9,314,154.

(60) Provisional application No. 61/548,152, filed on Oct. 17, 2011.

(51) Int. Cl.
*A61B 3/024* (2006.01)
*A61B 3/18* (2006.01)
*G16H 40/67* (2018.01)
*G16H 80/00* (2018.01)
*A61B 3/032* (2006.01)
*A61B 3/06* (2006.01)
*A61B 5/00* (2006.01)

(52) U.S. Cl.
CPC ............. *A61B 3/022* (2013.01); *A61B 3/024* (2013.01); *A61B 3/032* (2013.01); *A61B 3/06* (2013.01); *A61B 3/18* (2013.01); *A61B 5/7275* (2013.01); *G16H 40/67* (2018.01); *G16H 80/00* (2018.01)

(58) Field of Classification Search
CPC ........... A61B 3/06; A61B 3/18; A61B 5/7275; G16H 40/67; G16H 50/70; G16H 80/00
See application file for complete search history.

(56) References Cited

U.S. PATENT DOCUMENTS

| | | | |
|---|---|---|---|
| 4,798,456 A | 1/1989 | Enoch et al. |
| 5,129,720 A | 7/1992 | Jovicevic |
| 5,565,949 A | 10/1996 | Kasha |
| 5,568,209 A | 10/1996 | Priester et al. |
| 5,589,897 A | 12/1996 | Sinclair et al. |
| 5,596,379 A | 1/1997 | Kawesch |
| 5,880,814 A | 3/1999 | McKnight et al. |
| 5,892,570 A | 4/1999 | Stevens |
| 5,941,874 A | 8/1999 | Hohla |
| 6,033,076 A | 3/2000 | Braeuning et al. |
| 6,142,631 A | 11/2000 | Murdoch et al. |
| 6,425,665 B2 | 7/2002 | Hayashi et al. |
| 6,585,376 B1 | 7/2003 | Matsumoto |
| 6,656,131 B2 | 12/2003 | Alster et al. |
| 7,220,000 B2 | 5/2007 | Alster et al. |
| 7,275,830 B2 | 10/2007 | Alster et al. |
| 7,357,508 B2 | 4/2008 | Suzuki |
| 7,367,671 B2 | 5/2008 | Sabel |
| 7,427,137 B2 | 9/2008 | Koppany |
| 7,470,026 B2 | 12/2008 | Kaido et al. |
| 7,520,611 B2 | 4/2009 | Franz et al. |
| 7,665,847 B2 | 2/2010 | Alster et al. |
| 7,748,846 B2 | 7/2010 | Todd |
| 7,891,813 B2 | 2/2011 | Ogilvie |
| 7,942,529 B2 | 5/2011 | Tanassi et al. |
| 8,029,138 B2 | 10/2011 | Todd |
| 8,047,652 B1 | 11/2011 | Collazo |
| 8,322,857 B2 | 12/2012 | Barbur et al. |
| 8,523,360 B2 | 9/2013 | Husain |
| 8,702,238 B2 | 4/2014 | Berry et al. |
| 8,793,142 B2 | 7/2014 | Fishman et al. |
| 8,851,678 B2 | 10/2014 | Pelah et al. |
| 8,881,058 B2 | 11/2014 | Ollivierre et al. |
| 8,888,288 B2 | 11/2014 | Iravani et al. |
| 9,314,154 B2 | 4/2016 | Palanker et al. |
| 9,462,941 B2 | 10/2016 | Palanker |
| 9,572,484 B2 | 2/2017 | Palanker et al. |
| 10,702,140 B2 | 7/2020 | Palanker et al. |
| 2005/0124375 A1 | 6/2005 | Nowosielski |
| 2007/0146631 A1 | 6/2007 | Sinclair et al. |
| 2008/0309879 A1 | 12/2008 | Hirji |
| 2009/0060287 A1 | 3/2009 | Hyde et al. |
| 2011/0082704 A1 | 4/2011 | Blum |
| 2011/0170068 A1 | 7/2011 | Dan-Gur |
| 2011/0267577 A1 | 11/2011 | Verma |
| 2012/0050685 A1 | 3/2012 | Bartlett et al. |
| 2012/0050686 A1 | 3/2012 | Bartlett et al. |
| 2012/0218285 A1 | 8/2012 | Crane |
| 2012/0287163 A1 | 11/2012 | Djavaherian |
| 2013/0083185 A1 | 4/2013 | Coleman |
| 2013/0128229 A1 | 5/2013 | Huang |
| 2013/0155376 A1 | 6/2013 | Huang et al. |
| 2013/0194317 A1 | 8/2013 | Guillon et al. |
| 2013/0235346 A1 | 9/2013 | Huang et al. |
| 2013/0250246 A1 | 9/2013 | Shapiro |
| 2013/0278895 A1 | 10/2013 | Pham et al. |
| 2013/0301007 A1 | 11/2013 | Wolffsohn et al. |
| 2014/0114208 A1 | 4/2014 | Smith et al. |
| 2014/0132932 A1 | 5/2014 | Jung |
| 2014/0285768 A1 | 9/2014 | Barnard et al. |
| 2016/0374551 A1 | 12/2016 | Palanker |

FOREIGN PATENT DOCUMENTS

| | | |
|---|---|---|
| KR | 1020050114861 A | 12/2005 |
| KR | 1020060066967 A | 6/2006 |
| WO | WO2013/078406 A1 | 5/2013 |
| WO | WO2013/155002 A1 | 10/2013 |
| WO | WO2013/170091 A1 | 11/2013 |

OTHER PUBLICATIONS

Dok LLC; Eye chart professional (iTunes App Store); released Nov. 10, 2010; retrieved Dec. 9, 2014 from the internet (https://itunes. appie.com/us/app/id401851376?mt=8).

Fuso Precision; Amsler (iTunes App Store); released Oct. 28, 2010; retrieved Dec. 9, 2014 from the internet (https://itunes.apple.com/us/app/amsler/id396044848?mt=8).

Nead; Eyes Test (iTunes App Store); released Jan. 17, 2011; retrieved Dec. 9, 2014 from the internet (https://itunes.apple.com/us/app/eyestest/id414652461?mt=8).

Notal Vision; A modern alternative to the Amsler Grid (product information); ©2011; 2 pgs. (retrieved from the internet: http://www.notalvision.com/amsler_grid.html): This web address was available to applicant(s) at least as of Sep. 28, 2012.

Notal Vision; The ForseeHome age-related macular degeneration monitoring process (product information); ©2011; 2 pgs. (retrieved from the internet: http://www.notalvision.com/how_foresee_program_works.html); This web address was available to applicant(s) at least as of Sep. 28, 2012.

Notal Vision; The technology behind the ForseeHome AMD monitor (product information); ©2011; 2 pgs. (retrieved from the internet: http://www.notalvision.com/foresee-home-technology.html); This web address was available to applicant(s) at least as of Sep. 28, 2012.

Sabina Technology, LLP; Macula Tester (iTunes App Store); released Feb. 15, 2010; retrieved Dec. 9, 2014 from the internet (https://itunes.apple.com/us/app/maculatester/id334312308?mt=8).

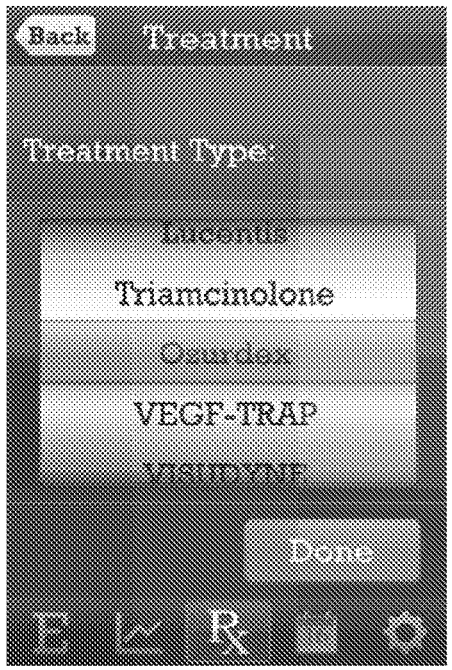
FIGURE 9A
FIGURE 9B
FIGURE 9C
FIGURE 9D

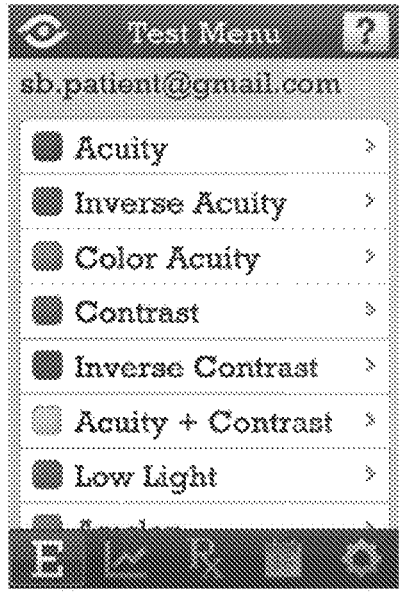
FIGURE 11A
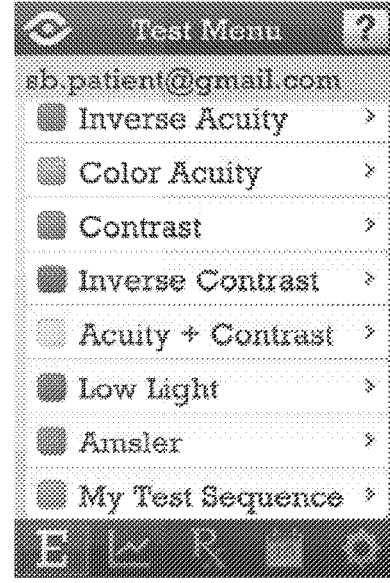
FIGURE 11B
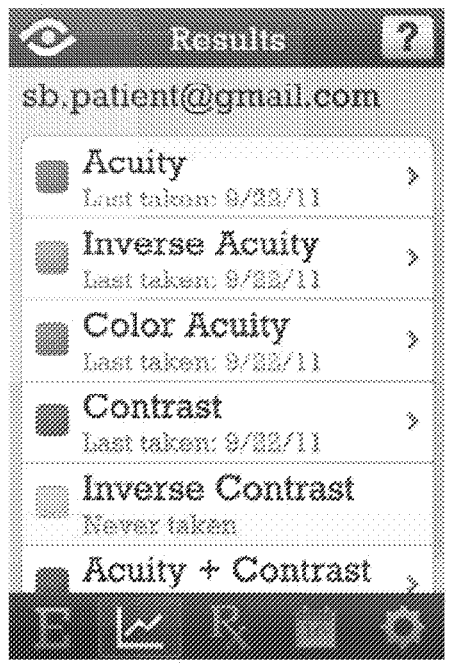
FIGURE 11C
FIGURE 11D

SYSTEM AND METHOD FOR PROVIDING ANALYSIS OF VISUAL FUNCTION USING A MOBILE DEVICE WITH DISPLAY

CROSS REFERENCE TO RELATED APPLICATIONS

This application is a continuation of U.S. patent application Ser. No. 15/424,733, filed Feb. 3, 2017, titled "SYSTEM AND METHOD FOR PROVIDING ANALYSIS OF VISUAL FUNCTION USING A MOBILE DEVICE WITH DISPLAY," now U.S. Pat. No. 10,702,140, which is a continuation of U.S. patent application Ser. No. 15/090,080, filed Apr. 4, 2016, titled "SYSTEM AND METHOD FOR PROVIDING ANALYSIS OF VISUAL FUNCTION USING A MOBILE DEVICE WITH DISPLAY," now U.S. Pat. No. 9,572,484, which is a continuation of U.S. patent application Ser. No. 14/352,571, filed Apr. 17, 2014, titled "SYSTEM AND METHOD FOR PROVIDING ANALYSIS OF VISUAL FUNCTION USING A MOBILE DEVICE WITH DISPLAY," now U.S. Pat. No. 9,314,154, which is a 35 U.S.C. § 371 application of International Patent Application No. PCT/US2012/060627, filed Oct. 17, 2012, titled "SYSTEM AND METHOD FOR PROVIDING ANALYSIS OF VISUAL FUNCTION USING A MOBILE DEVICE WITH DISPLAY," Publication No. WO 2013/059331 A1, which claims the benefit of provisional application No. 61/548,152, filed Oct. 17, 2011, titled "SYSTEM AND METHOD FOR PROVIDING ANALYSIS OF VISUAL FUNCTION USING A MOBILE DEVICE WITH DISPLAY," each of which is incorporated herein by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to a system for analysis of visual function of a person using a mobile device with a display and communication capability, and method of use thereof. In various respects, the invention is directed to a system that allows patients to monitor their vision using a mobile device, manage treatment and therapy, and streamline communications between patients, physicians and healthcare providers.

BACKGROUND

Many different diseases may result in vision loss and even blindness, if not promptly recognized and treated. Vision loss associated with retinal diseases typically involves several important symptoms including image distortion, decrease in visual acuity, loss of contrast discrimination, especially in low lighting conditions, holes or defects in the visual field, or inability to accurately distinguish colors.

Severity of symptoms is typically highly correlated with the stage of the disease, and generally, earlier diagnosis and treatment improve the potential for a good outcome. Important changes in the visual function can be quantified by the vision tests, which have been historically administered in the offices of eye physicians and optometrists.

Availability of new tools for the treatment of retinal diseases, particularly a class of compounds called VEGF inhibitors (Lucentis and Avastin) have dramatically improved the therapeutic outcomes. However, every patient is different with respect to the optimum dose and frequency of these treatments. Without frequent measurements of vision to monitor disease progression some patients may be under-treated, while others over-treated. Under-treatment can lead to severe and irreversible disease progression and associated loss of vision. Over-treatment is expensive, uncomfortable and potentially increases the risk of complications.

A single test in the doctor's office provides only one snapshot of the visual function, and may be a subject to random fluctuation of vision. Frequent testing of vision using a variety of tests will allow detecting trends in the visual function with much higher precision than a single test can provide. As a result, there is a need in the art for improved analysis of visual function.

SUMMARY OF THE DISCLOSURE

Methods are disclosed herein for performing a visual function evaluation of a patient with a retinal disease. The patient can be under recurrent treatment. The methods include executing a patient administered visual function evaluation on a mobile device. The evaluation can include one or more visual function tests pre-selected by a healthcare provider. Each visual function test can be comprised of a number of steps and the difficulty of a subsequent step is based on a patient's response to a previous step within the test. The methods include indicating at least one response to a pre-selected visual function test using a touch screen on the mobile device.

The one or more tests can be selected by the healthcare provider by direct communication with the patient or using a remote server with the selection of the one or more tests transmitted to the patient's mobile device. The visual function tests can be pre-selected by the healthcare provider patient based on patient-specific, disease-specific, or treatment-specific criteria. The visual function tests can be pre-selected by the healthcare provider based on the retinal disease or based on the recurrent treatment. The recurrent treatment can include monitoring disease progression, administration of a pharmacological agent, a laser treatment, visiting a healthcare provider to determine the need for further treatment. The recurrent treatment can be administered by a healthcare provider, including a physician or doctor.

The methods can include transmitting the visual function evaluation results from the mobile device to a remote server. The methods can include analyzing the results of the visual function evaluation using the remote server to determine if a next treatment is to be scheduled. The remote server can implement an automated analysis of the results of the visual function evaluation to determine trends in the patient's visual function based on the most recent results and previous data.

Examples of visual function tests include visual acuity, contrast sensitivity, low luminance vision, color vision, perimetry, and distortion in the visual field. The visual function test can include an adjustable difficulty level. For example, a level of difficulty for a subsequent step can be higher than a level of difficulty for a previous step when the patient enters a correct response in the previous step. The level of difficulty for the subsequent step can be lower than the level of difficulty in the previous step when the patient enters an incorrect response in the previous step. The visual acuity can be measured by sequentially displaying fonts of various sizes and offering a multiple choice of fonts for a matching selection.

Methods are also disclosed herein for performing an analysis of a visual function of a user with a retinal disease who is receiving recurrent treatment from a healthcare provider. The methods include receiving the user's visual function test data from a remote mobile device application and executing a test data analysis module stored in memory by a processor. The executed test data analysis module can process the visual function test data to generate a trend data of visual function. The data analysis module can analyze the trend data of visual function based on the retinal disease of the user to determine the user's response to treatment, need for treatment, or need for evaluation by a healthcare provider. The visual function test data and the trend data can be transmitted to a remote computing device.

The methods can include predicting a time for the next treatment for the user based on the trend data of visual function. The methods can include analyzing the trend data of visual function and comparing the trend data to previous trend data for the user. The methods can include transmitting an alert to the remote computing device if the trend data of visual function is outside of a range of acceptable variation in comparison to the previous trend data for the user. The methods can include making the visual function test data and the trend data available to the healthcare provider.

Systems for performing a visual function analysis are disclosed herein. The systems include a processor, a memory, a test data analysis module stored in memory and executable by the processor to generate trend data from visual function test data received from a remote mobile device associated with a user having a retinal disease and receiving recurrent treatment from a healthcare provider and an I/O interface module stored in memory and executable by the processor to send trend data and a physician message to the remote mobile device. The visual function test data can correspond to tests that were pre-selected for the user by the user's healthcare provider and performed by the user using the remote mobile device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A-9D illustrate screenshots of an interface for managing treatment data.

FIGS. 11A-11D illustrate screenshots of an interface for managing test data.

DETAILED DESCRIPTION

Figure 1A:
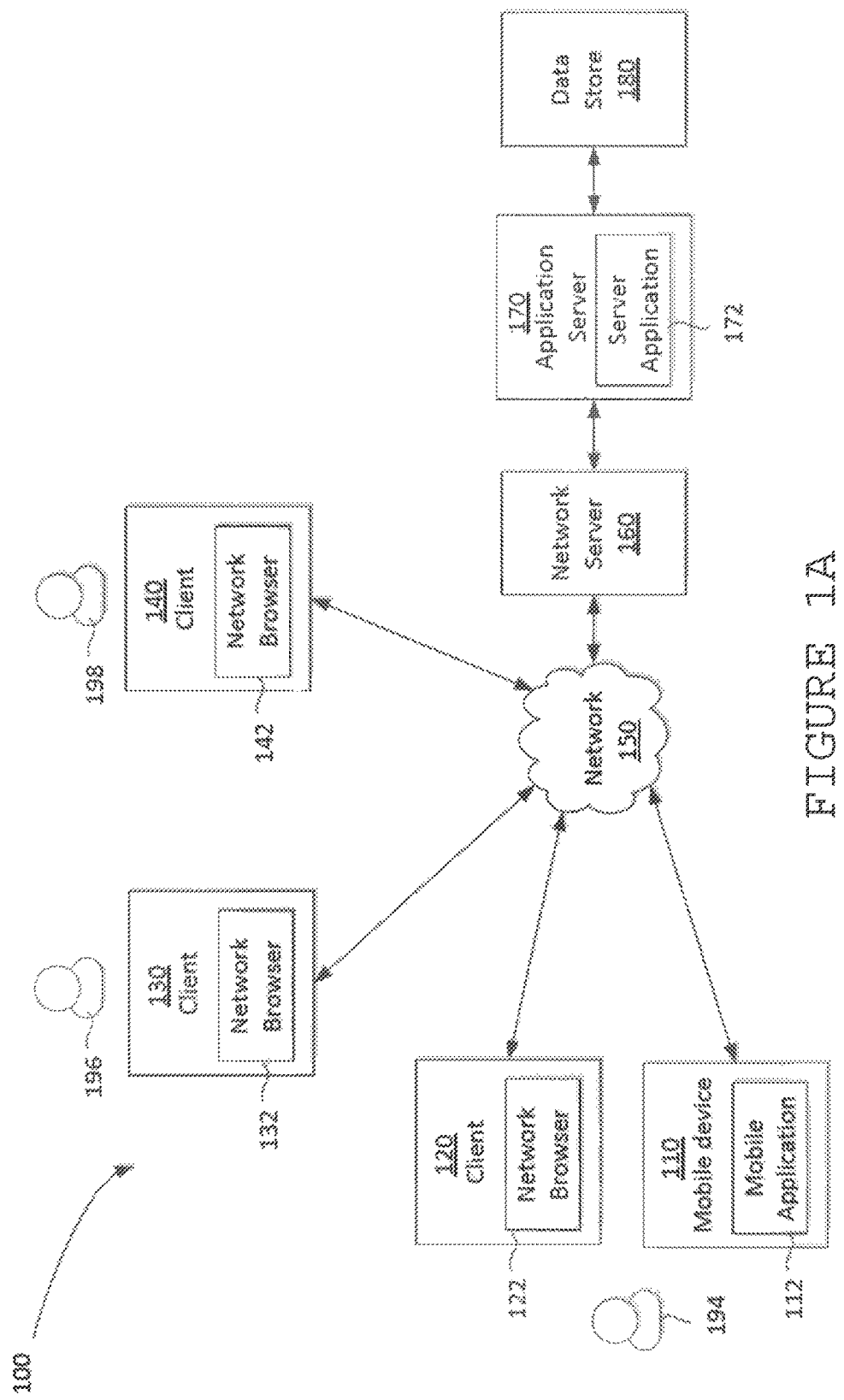
FIG. 1A is a block diagram of an exemplary system to implement a visual function analysis system.

Methods, devices, and systems for evaluating the visual function of user are disclosed herein. The visual function evaluation of the patient can include one or more visual function tests. The systems and methods for evaluating visual function can be used with a mobile device with a display. The mobile device may electronically communicate with a network service, such as a web service, through a combination of cellular networks and other networks. A patient user may perform a variety of visual tests using the mobile device. The mobile device transmits the test results to a remote server implementing an analysis network service. The network service receives the test results, processes the results, and provides the processed results to a physician. The processed results may include trends of the user's test performance, variation of various measures of visual function over time (acuity, contrast, color, distortions etc.).

The trend for a visual function test is a patient's performance for that test over a period of time. The period of time may be an hour, a day, a week, a month, or any other period of time. Trend data for a visual function test may include two or more data points generated by the test at different times by the user. For example, if a user takes a visual acuity test once a month for one year, the trend data will include twelve data points which can be used to form a trend.

The healthcare provider may optimize and administer treatment based on the data in a timely manner. Early detection of changes in visual function may empower patients and enable their physicians to individualize treatment, helping to prevent vision loss while minimizing visits to the office, discomfort and expense. Hence, regular testing may help to identify changes in vision and track them over time. Tracking changes over time may, in turn, help physicians optimize treatment of a preexisting eye condition or diagnose a new problem earlier.

The trend data for visual function can be useful to the healthcare provider to improve the effectiveness and timing for patient treatment. The trend data can be used to predict the need for additional treatment for the patient. Patients can respond differently to periodic treatments. Analysis of the trend data for the patient can improve the effectiveness of the treatment by tailoring the timing between treatments for the individual patient.

Tailoring the timing of the recurrent treatment can have advantages for both the healthcare provider and patient. It can be difficult for patients with ophthalmic problems to arrange travel for appointments. Optimizing the timing for recurrent treatments can reduce the inconvenience for the patient traveling to appointments. Appointments for recurrent treatment are often set at a regular interval. In some cases the patient can have regularly scheduled appointments for a recurrent treatment and not exhibit a decrease in visual function or symptoms typically treated by the recurrent treatment. The office visit may not be useful for the patient and also take up additional time of the healthcare provider. Moreover, the decrease in visual function or symptoms in the patient may arise shortly after the appointment and require scheduling an appointment on short notice for additional treatment. The trend data can allow for tailoring the timing of treatments for the patient, thereby improving the effectiveness of the treatment by the healthcare provider and minimizing inefficient use of the patient's time and the healthcare provider's time.

Analysis of the trends in the patient's visual function can also provide early alerts to the healthcare provider and patient of a possible change in the visual function of the patient. The alert can allow for early and preventative treatment for the patient to prevent additional loss in visual function.

The patient can be under recurrent treatment administered by a healthcare provider. The healthcare provider can include a doctor, physician, nurse, medical technician, or other medical professional. In some cases the recurrent treatment is administered by a doctor or physician.

The recurrent treatment can include any type of treatment from a healthcare provider. In some embodiments the recurrent treatment can include monitoring disease progression in the patient. In some embodiments the recurrent treatment can include administration of a pharmacological agent. In some embodiments the recurrent treatment can be a laser treatment. In some embodiments recurrent treatment can include an intraocular injection of a pharmacological agent. Examples of pharmacological agents include VEGF inhibitors such as Lucentis and Avastin.

In some embodiments recurrent treatment can include visiting a physician's office and conducting testing under the guidance of a healthcare provider. The visit to the physician's office can be used to determine whether the patient has a need for additional treatment. In some embodiments recurrent treatment can include retinal imaging. The retinal images can be analyzed to determine the need for further treatment.

An evaluation of the visual function of the patient can include one or more visual function tests. Examples of visual function tests include visual acuity, contrast sensitivity, low luminance vision, color vision, perimetry, and distortion in the visual field.

The visual function tests can be pre-selected from a list of available vision tests by the healthcare provider. For example, the physician or doctor treating the patient can select which of the visual function test or tests stored on the mobile device for the patient to take. The doctor can select the visual function tests that are relevant for the specific patient. The healthcare provider can upload the selection to a server. The selection of test or tests can be sent from the server to the patient's mobile device. The patient can then be automatically directed to take the selected test or tests on their mobile device.

The visual function test or tests can be pre-selected by the healthcare provider based on a number of factors. The visual function test can be selected by the healthcare provider based on patient specific, disease specific, or treatment specific criteria. The visual function test can be selected based on the patient's retinal disease. The visual function test can be selected based on the results of retinal imaging of the patient. The visual function test can be selected based on the recurrent treatment that the patient receives. For example, a distortion test can be selected for a patient with dry macular degeneration disease to test for progression to a wet macular degeneration disease. A distortion test (metamorphopsia) can be prescribed to monitor development of a diabetic macular edema.

The frequency of the visual function evaluation can be set by the healthcare provider. The frequency for individual tests within the visual function evaluation can also be set by the healthcare provider. The frequency of the testing can be initially set to a default setting. The healthcare provider can change the frequency after reviewing the patient's responses during a monitoring period or after reviewing trends in the patient's visual function. The frequency can also be set by analyzing the trend data for the user.

The methods and systems disclosed herein can be useful for patients having a number of retinal disease and ophthalmic disorders. Examples of retinal disease include macular degeneration, diabetic retinopathy, diabetic macular edema, retinal vein occlusion, glaucoma, and chronic retinal detachment. Examples of macular degeneration include dry macular degeneration and wet macular degeneration.

The visual function tests can be stored and displayed on the mobile device. The patient (user) can input the answers to the tests by touching a touch screen on the mobile device. The patient can also make an audible response to the tests.

The visual function tests are disclosed in greater detail below. In general, the visual function tests can have an adjustable difficulty level based on previous test responses. The difficulty level of the next step in the visual function test can be at a lower level of difficulty if the patient incorrectly answers the test question. The difficulty level of the next step in the visual function test can be at a higher level of difficulty if the patient correctly answers the test question.

In some cases the visual function tests can end once a question at a specified level of difficulty has been reached. In some cases the test can end after multiple correct responses have been entered at one level of difficulty with multiple incorrect responses at the next higher level of difficulty. The progression of test steps and difficulty of the steps can be adjusted based on the methods and algorithms disclosed herein.

The results of the visual function evaluation and individual tests can be sent to a remote server for analysis of the data. The remote server can be used to analyze the visual function test data. The remote server can implement an automated analysis of the results of the visual function evaluation to determine trends in the patient's visual function based on the recent results and previous data. The server can analyze the visual function data to determine if a next treatment is to be scheduled for the patient.

The data analysis of the results of the visual function evaluation can include comparing the results to a baseline level of performance for the patient. The baseline level of performance for the patient can be determined from previous visual function evaluation and test results. The server can be configured to send an alert to the healthcare provider if the visual function test results deviate from the baseline level of performance above a delta level. The healthcare provider can specify the delta level.

The analysis by the remote server can include comparing the trends in the patient's visual function to trends for other patients or groups of other patients.

In some embodiments the results of the analysis of the patient's visual function can be provided to the healthcare provider. The results can be used to help determine whether there is a significant deterioration of the visual function that requires any treatment. The results can be made available on a secure webpage. The secure webpage can be accessed by the healthcare provider and/or user.

In some embodiments the remote server can instruct the mobile device application to automatically re-test the patient if the visual function evaluation or test result is outside of a range of acceptable variation for the patient. The healthcare provider can specify the range of acceptable variation for the patient. In some cases the remote server analysis can analyze the past data for the patient to determine a range of acceptable variation for the patient.

In some embodiments the remote server can receive a message from the healthcare provider for the user and transmit the message to the remote computing device.

In some embodiments the analysis performed by the remote server can predict a time for the next treatment based on the trend in the user's visual function. The prediction can be transmitted to the remote computing device.

FIG. 1A is a block diagram of an exemplary system to implement a visual function analysis system. System 100 of FIG. 1 includes mobile device 110 and client device 120 associated with user 194, network 150, network server 160, application servers 170, and data store 180. The system of FIG. 1A also includes client 130 for physician or healthcare provider 196 and client 140 for third party 198. Though the discussion below may refer to a physician, a physician and a healthcare provider are intended to be interchangeable for the methods and systems disclosed herein.

Mobile device 110 may communicate with network 150 and includes mobile application 112. Mobile device 110 may receive input from a user and execute one or more programs to administer one or more tests to a user, provide test results to application server 170, and receive test set data, account data, and other data from application server 170. The user may be a patient of a physician associated client 130. The terms user and patient may be used interchangeably herein. Mobile device 110 is discussed in more detail with respect to FIG. 21.

Mobile application 112 resides in memory on mobile device 110 and may be executed to allow a user to setup and login to an account with a network service, administer test results, and perform other functions. More detail for mobile application 112 is discussed with respect to FIG. 2A.

Client device 120 may include network browser 122 and be implemented as a computing device, such as for example a laptop, desktop, workstation, or some other computing device. Network browser 122 may be a client application for viewing content provided by an application server, such as application server 170 via network server 160 over network 150.

Network 150 may facilitate communication of data between different servers, devices and machines. The network may be implemented as a private network, public network, intranet, the Internet, or a combination of these networks.

Network server 160 is connected to network 150 and may receive and process requests received over network 150. Network server 160 may be implemented as one or more servers implementing a network service. When network 150 is the Internet, network server 160 may be implemented as one or more web servers.

Application server 170 communicates with network server 160 via network server 160 and data store 180. Application server 170 may also communicate with other machines and devices (not illustrated in FIG. 1A). Application server 170 may host a server application 172, and other software modules. Application server 170 may be implemented as one server as illustrated in FIG. 1A or multiple servers.

Server application 172 may reside on application server 170 and may be executed to store, retrieve and transmit test set data, analyze test set results, and manage alerts. Server application 172 is discussed in more detail below with respect to FIG. 2B.

Data store 180 may be accessed by application server 170. Data store 170 may store data, process data, and return queries received from application server. Data stored on application data store 180 may include user account data, user test data, user test results, analysis of the results such as trend data, and other data.

Clients 130 and 140 and network browsers 132 and 142 may be similar to client 120 and network browser 122, except that clients 130 and 140 may be associated with a physician and a third party (such as a drug company), respectively, rather than a user (patient).

Figure 1B:
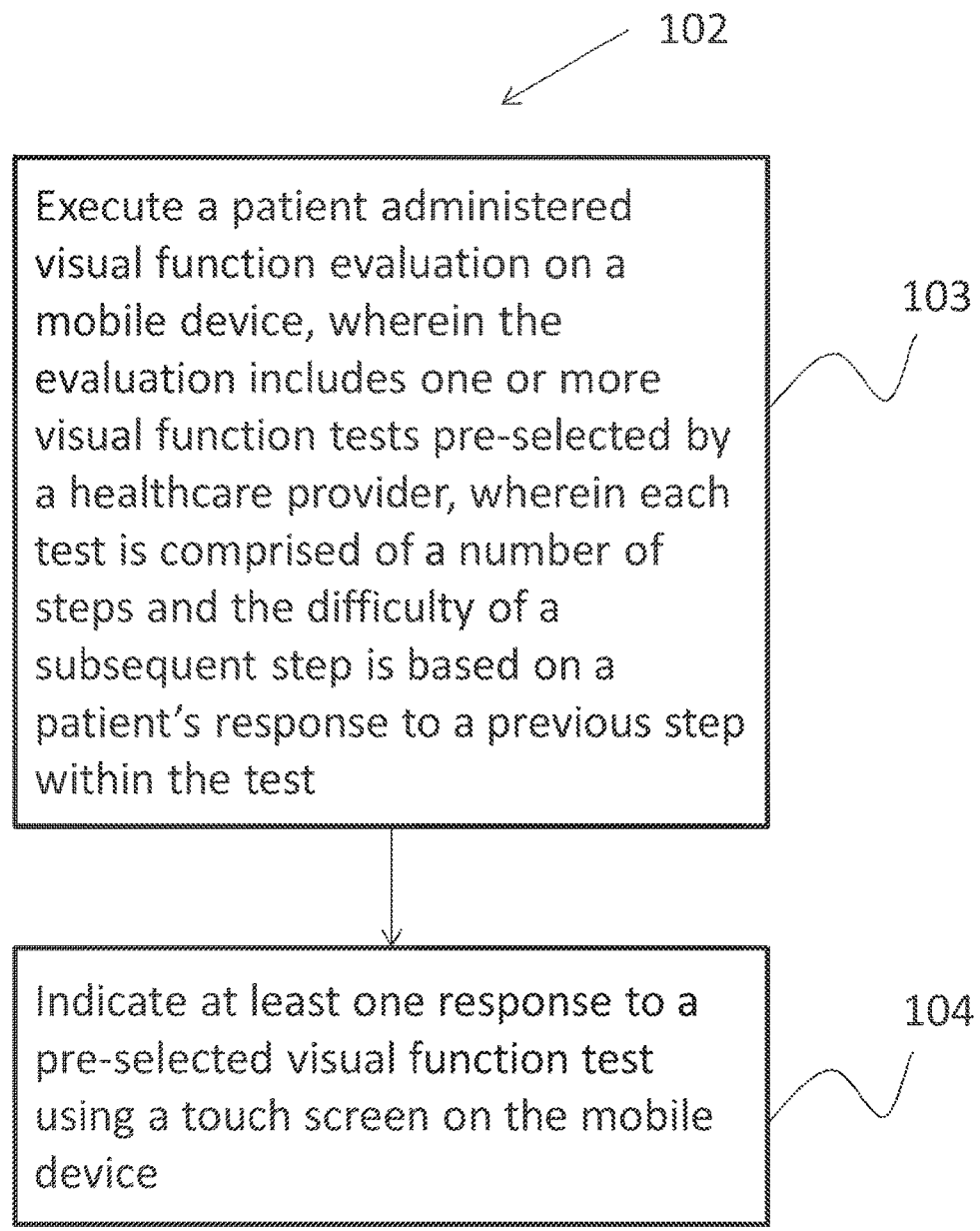
FIG. 1B is a flow chart of a method for performing a visual function evaluation of a patient.

FIG. 1B is a flow chart of a method 102 for performing a visual function evaluation of a patient in accordance with one embodiment. The method 102 includes executing a patient administered visual function evaluation on a mobile device 103. The visual function evaluation includes one or more visual function tests pre-selected by a healthcare provider. Each test is comprised of a number of steps and the difficulty of a subsequent step is based on a patient's response to a previous step within the test. The method 102 includes indicating at least one response to a pre-selected visual function test using a touch screen on the mobile device 104. The patient can have a retinal disease and be receiving a recurrent treatment from a healthcare provider.

The patient administered visual function evaluation on a mobile device can include one or more visual function tests pre-selected by a healthcare provider. The one or more tests can be selected by the healthcare provider using a remote server with the selection of the one or more tests transmitted to the patient's mobile device. The visual function tests can be pre-selected by the healthcare provider patient based on patient-specific, disease-specific, or treatment-specific criteria. The visual function tests can be pre-selected by the healthcare provider patient based on the retinal disease or based on the recurrent treatment. The recurrent treatment can include monitoring disease progression, administration of a pharmacological agent, visiting healthcare provider to determine the need for further treatment. The recurrent treatment can be administered by a healthcare provider, including a physician or doctor.

The methods can include transmitting the visual function evaluation results from the mobile device to a remote server. The methods can include analyzing the results of the visual function evaluation using the remote server to determine if a next treatment is to be scheduled. The remote server can implement an automated analysis of the results of the visual function evaluation to determine trends in the patient's visual function based on the most recent results and previous data.

Examples of visual function tests include visual acuity, contrast sensitivity, low luminance vision, color vision, perimetry, and distortion in the visual field. The visual functions test can include an adjustable difficulty level. For example, a level of difficulty for a subsequent step can be higher than a level of difficulty for a previous step when the patient enters a correct response in the previous step. The level of difficulty for the subsequent step can be lower than the level of difficulty in the previous step when the patient enters an incorrect response in the previous step. The visual acuity can be measured by sequentially displaying fonts of various sizes and offering a multiple choice of fonts for a matching selection.

Figure 1C:
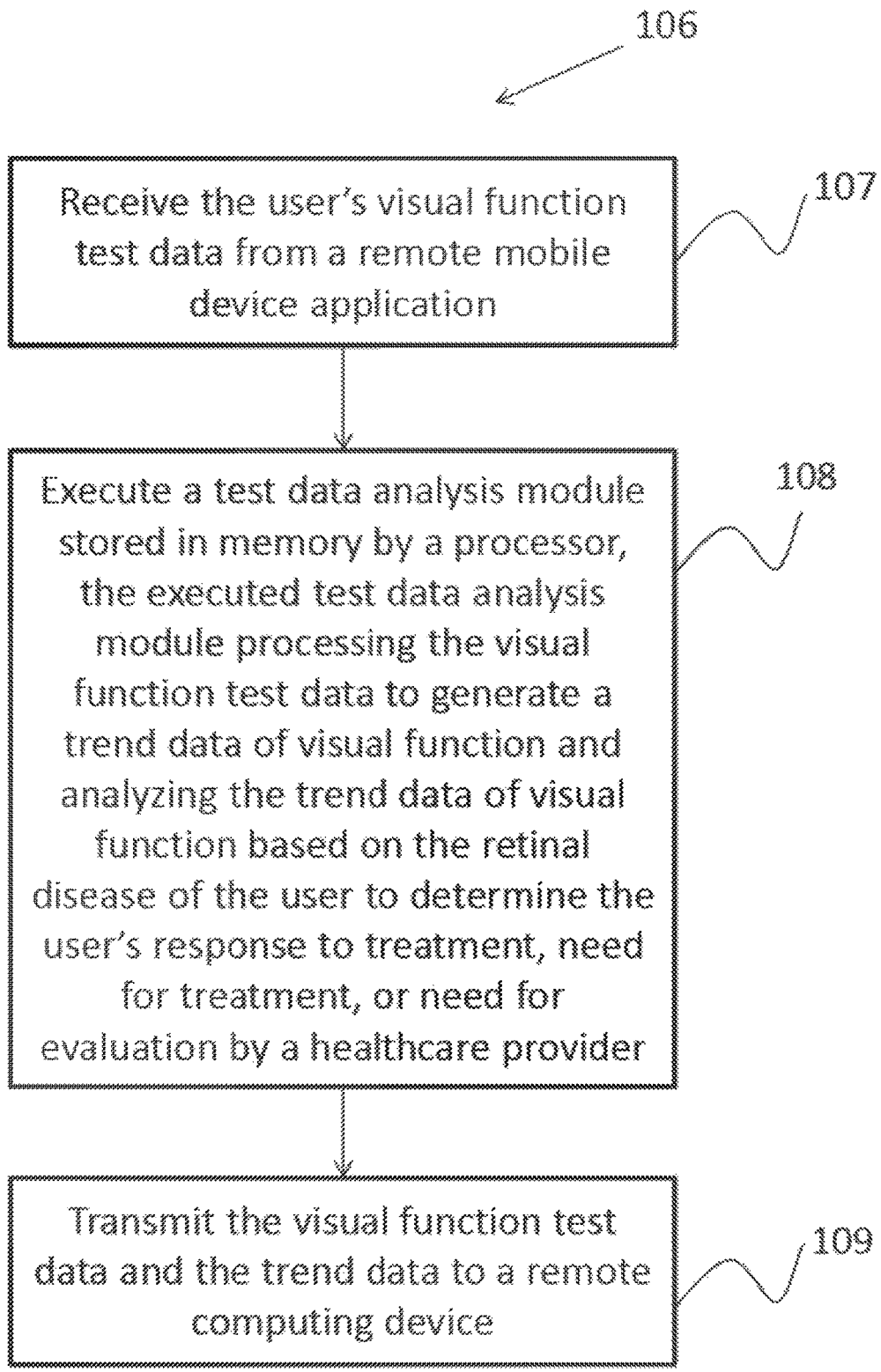
FIG. 1C is a flow chart of a method for performing an analysis of a visual function of a user.

FIG. 1C is a flow chart of a method 106 for performing an analysis of a visual function of a user in accordance with one embodiment. The user can have a retinal disease and be receiving recurrent treatment from a healthcare provider. The method 106 includes receiving the user's visual function test data from a remote mobile device application 107. The method 106 includes executing a test data analysis module stored in memory by a processor, the executed test data analysis module processing the visual function test data to generate a trend data of visual function and analyzing the trend data of visual function based on the retinal disease of the user to determine the user's response to treatment, need for treatment, or need for evaluation by a healthcare provider 108. The method 106 includes transmitting the visual function test data and the trend data to a remote computing device 109.

Figure 2A:
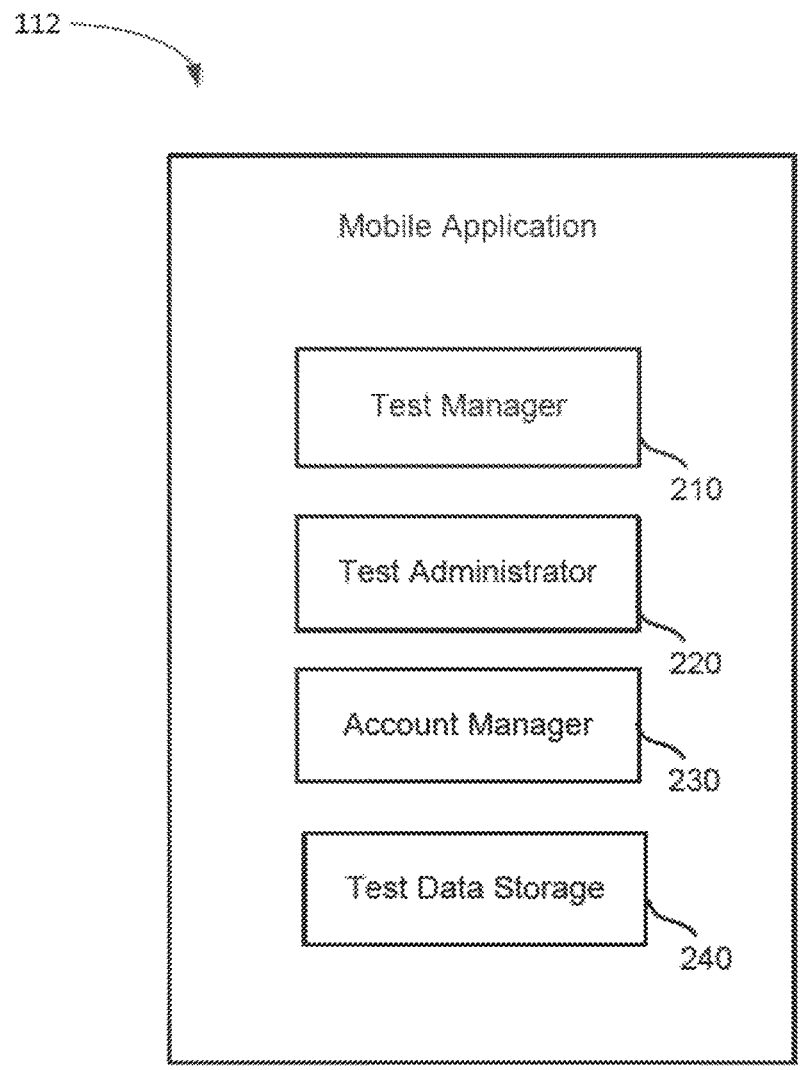
FIG. 2A is a block diagram of an exemplary mobile application.

FIG. 2A is a block diagram of an exemplary mobile application. Mobile application 112 may include a test manager module, test administrator module, account manager module, and a test data storage module. Each of modules 210-240 may be stored in memory on mobile device 110 and executed by a processor (see FIG. 21). The test manager module may configure test sets to be administered to a user. The test manager module may select tests to administer and configure each test as required or optional. The test set may be configured by the test manager module based on user input, instructions or other data provided by a physician, user settings and biographical data, and other data. In some embodiments the test set is selected by the physician for the specific patient. The pre-selected tests can be automatically administered when the mobile application is opened without the need for the patient/user to select the pre-selected tests from the list of all of the tests available on the mobile application.

The visual function test can be selected by the healthcare provider based on patient specific, disease specific, or treatment specific criteria. The visual function test can be selected based on the patient's retinal disease. The visual function test can be selected based on the results of retinal imaging of the patient. The visual function test can be selected based on the recurrent treatment that the patient receives.

Test administrator module 220 may administer one or more tests to a user through the mobile device 110. The tests may be administered as a set of tests. Each test in the test set may be administered by test administrator module 220 by graphic interfaces provided through a display system in the mobile device, as well as audio and other features of the mobile device.

Account manager module 230 may manage account data, account login, and other data for a user. The account manager module 230 may store local user account data, such as account identification, login credentials, user biographical information, and other data. Account manager module 230 may perform login with a network service on behalf of a user.

Test data storage 240 may store test data and other data on mobile device 110. The test data may include past test results, the test to administer to a user as part of a test set visual function evaluation, and other test data.

Figure 2B:
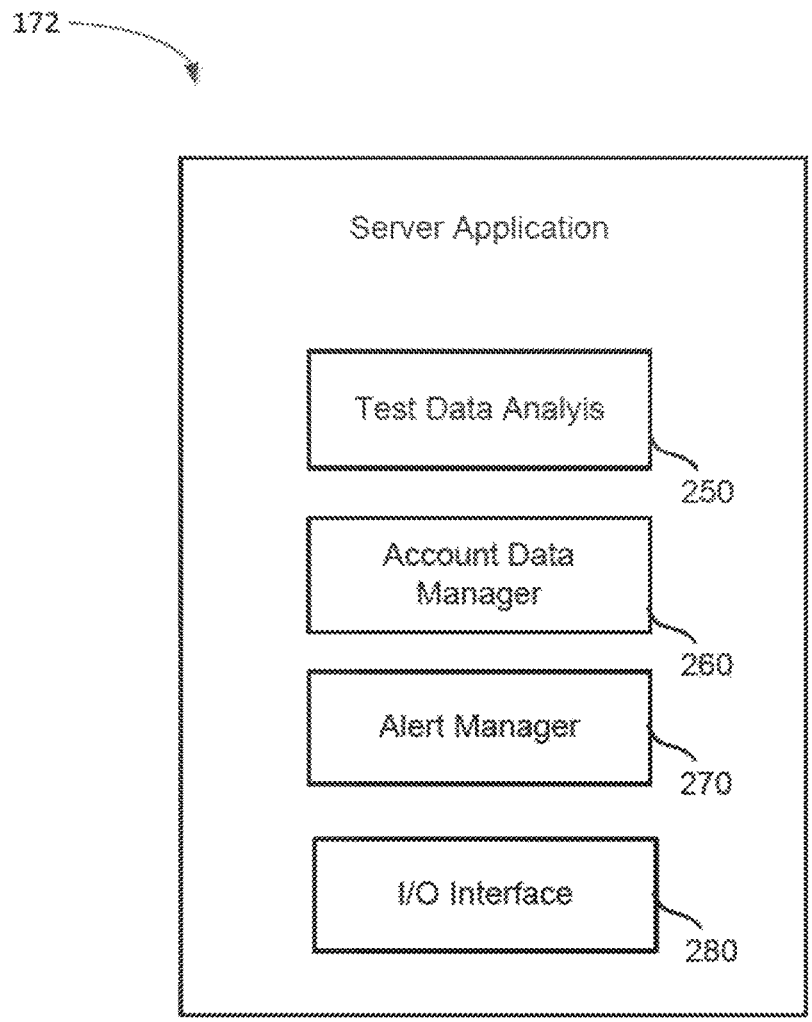
FIG. 2B is a block diagram of an exemplary server application.

FIG. 2B is a block diagram of an exemplary server application. Server application 172 resides on application server 170 and may include test data analysis module 250, account data manager module 260, alert manager module 270, and I/O Interface module 280. Each module may be stored in memory on application server 170 and executed by one or more processors on application server 170 (see FIG. 22). Test data analysis module 250 may be executed to analyze test data results. The test data results can be received from a remote mobile device associated with a user with a retinal disease. The test data can include results for a user receiving recurrent treatment from a healthcare provider. The visual function tests can be pre-selected by the healthcare provider for the user, with the pre-selected tests sent to the user's remote mobile device.

Analysis of test data results may include identifying long-term trends in test result data and identifying whether the trend represents an undesirable condition or requires further investigation. Account data manager module 260 may be executed to manage user account data, including update user account information stored on the application server. Alert manager module 270 may be executed on application server 170 to create, configure, modify and process alerts. For example, alert manager module 270 may be configured to generate an alert message to a physician if a user (patient) long-term trend data matches a profile for a particular eye disease or disorder. I/O Interface module 280 may handle receipt and transmittal of data to and from mobile device 110 and client device 130, as well as communication between server application 170 and other devices and applications.

The test data analysis module can analyze the test data to determine trends in the user's data. The data analysis can include comparing the recent test data for the user to past results. The past results can be from anytime in the past, for example the past day, week, month, or year.

The trends in the user data can be compared to trends for other users or trend data grouped together for other users. For example, the trends in the user data can be compared to trend data for other users with similar retinal diseases.

The data analysis can include determining a baseline level of performance for the user based on the user's previous test data. The healthcare provider can specify a delta level for the user. The data analysis can include analyzing the difference between recent test data and the user's baseline level of performance. If the difference between the recent test data and the baseline is above the specified delta then an alert can be sent to the user and the healthcare provider.

In some embodiments the baseline for the user can include the average test results for the user between recurrent treatments, such as an intraocular injection. The user's vision between the injections can be used to develop the baseline. An alert can be sent to the user and patient if the test data deviates from the baseline, which could indicate a problem with the user's vision that could require evaluation by the healthcare provider or a treatment like an intraocular injection.

In some embodiments, the test data analysis can be used to predict the time for the next treatment. For example, the test data can be analyzed and compared to previous data for the patient to determine an estimate for the next intraocular injection for the user.

The data analysis can include determining an acceptable level of variation for the user. The level of variation can also be set by the healthcare provider. An automatic retest can be sent to the user for test data that exceeds the acceptable level of variation. The user can then retake the visual function test.

The modules of mobile application 112 and server application 172 are exemplary. Mobile application 112 and server application 172 may each contain additional or fewer modules and each module may contain one or more sub-modules or be combined with one or more other modules.

Figure 3:
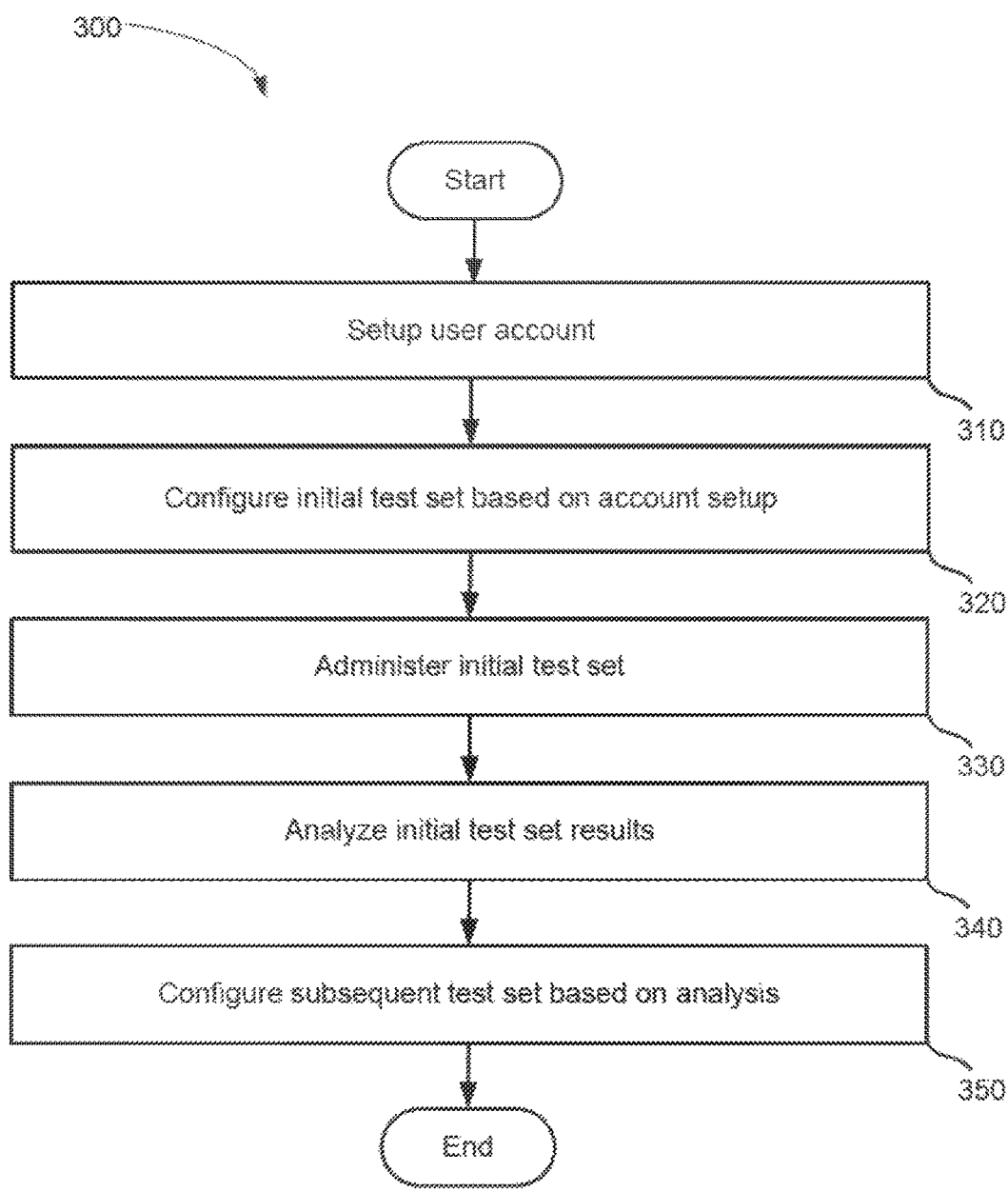
FIG. 3 is a flow chart of a method for performing an analysis of visual function of a person using a mobile device.

FIG. 3 is a flow chart of a method for performing analysis of visual function of a person using a mobile device. A user account is setup for a user (patient) at step 310. The user account may be set-up from either mobile device 110 or client device 120. Setting up a user account may include performing login, creating a new account, and entering account data. More detail for setting-up a user account is discussed below with respect to FIG. 4.

An initial test set can be configured based on the account set-up at step 320. The initial test set includes the list of tests to administer to the patient. The initial test set may be set by a physician after viewing the user account data, selected by the user, or automatically configured for the user. In various embodiments, the initial test may be automatically configured based on the patient's biographical data, diagnosis, or other disease characteristics.

The initial test set is administered to the user at step 330. The tests of the initial test set may be administered through mobile device 110 by test administrator 220. The tests administered to the user may include visual acuity, inverse acuity, inverse contrast, combination of acuity and contrast, low light conditions, color, low light contrast, low light acuity, perimetry, distortion in the visual field, low luminance vision, Amsler grid, and other tests. Administering tests is described in more detail below with respect to FIGS. 5A-B. Information regarding tests which can be administered to a user is described in more detail below with respect to FIGS. 12-19.

Initial test set results are analyzed at step 340. The analysis may include calculating a trend and determining if the trend is associated with or suggests a stable condition, the possibility of an undesirable condition, or improvement. The results of the analysis may be used by the user (patient) or the physician to monitor the user's visual function as a state of a user's current vision-related disease. In various embodiments, a user may monitor analysis results using the mobile application. In various embodiments, the analysis of the test set results may be performed by server application 172. Analyzing initial test results is discussed in more detail below with respect to FIG. 6.

A subsequent test set is configured for the patient at step 350. The subsequent test set may be configured based on results from a prior administered test set, physician recommendations, and user preferences. Configuring a subsequent test set may also include configuring an appointment for the user, prescribing a treatment, and dose reminders. Configuring a subsequent test set is described in more detail below with respect to FIG. 7.

Figure 4:
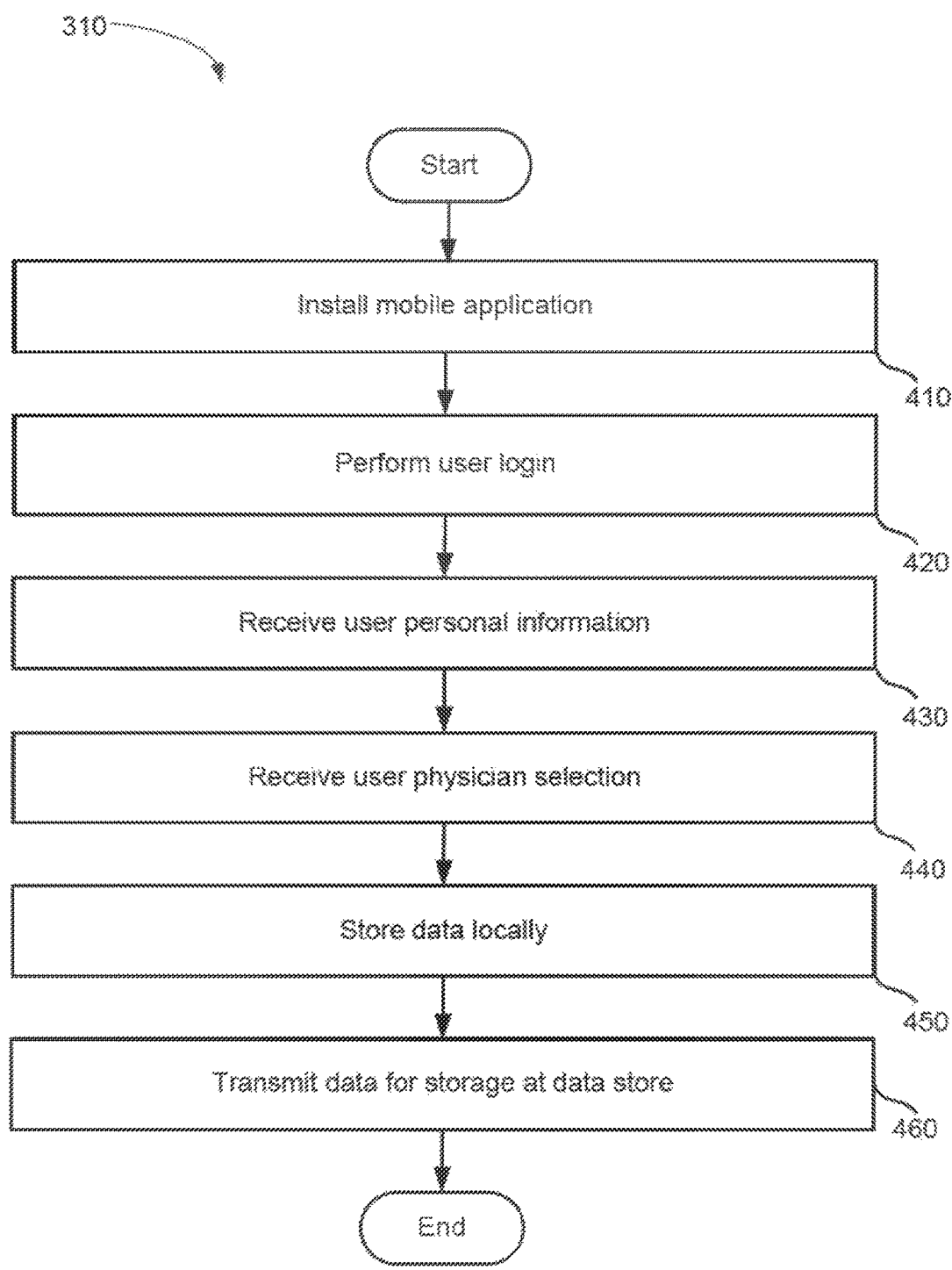
FIG. 4 is a flow chart of a method for setting-up a user account.

FIG. 4 is a flow chart of a method for setting-up a user account. The method of FIG. 4 provides more detail for step 310 of the method of FIG. 3 and may be performed at either mobile device 110, client 120, or a combination of these. A mobile application may be installed on mobile device 110 at step 410. The mobile application may be downloaded via cable or wirelessly to the mobile device, installed by a manufacturer, or installed in some other manner. A user login may be performed at step 420. At the first login for the user, login credentials may be created for the user. Upon subsequent logins, the user login information is used to log the user into the network service. Typically, a login includes a username and a password for the user.

Personal information may be received from the user at step 430. The personal information may include user address, phone, email, sex, age, health data, diagnosis data, treatment data and other data. The personal information may be received initially, gradually over time, and/or changed by a user.

A physician selection may be received at step 440. In some cases the user can select a physician to review his or her test set results and other medical data. By selecting a physician, the user grants the physician permission to access the user's account with the visual analysis service. The personal information and physician selection data may be stored locally, at either the mobile device 110 or client 120, at step 450. The personal information and physician selection data may be transmitted to data store 180 via network 150, network server 160, and application server 170 at step 460.

The physician selection or pre-selected tests can be made by the healthcare provider, including the physician, doctor, nurse, medical professional, or medical technician. In some cases the physician selection can be selected by the doctor or physician and entered into the system by a medical professional, medical technician, or nurse. The pre-selected tests can be selected by the healthcare provider using a remote server with the selection transmitted to the patient's mobile device. The physician selection can be based on any of the patient criteria disclosed herein.

Figure 5A:
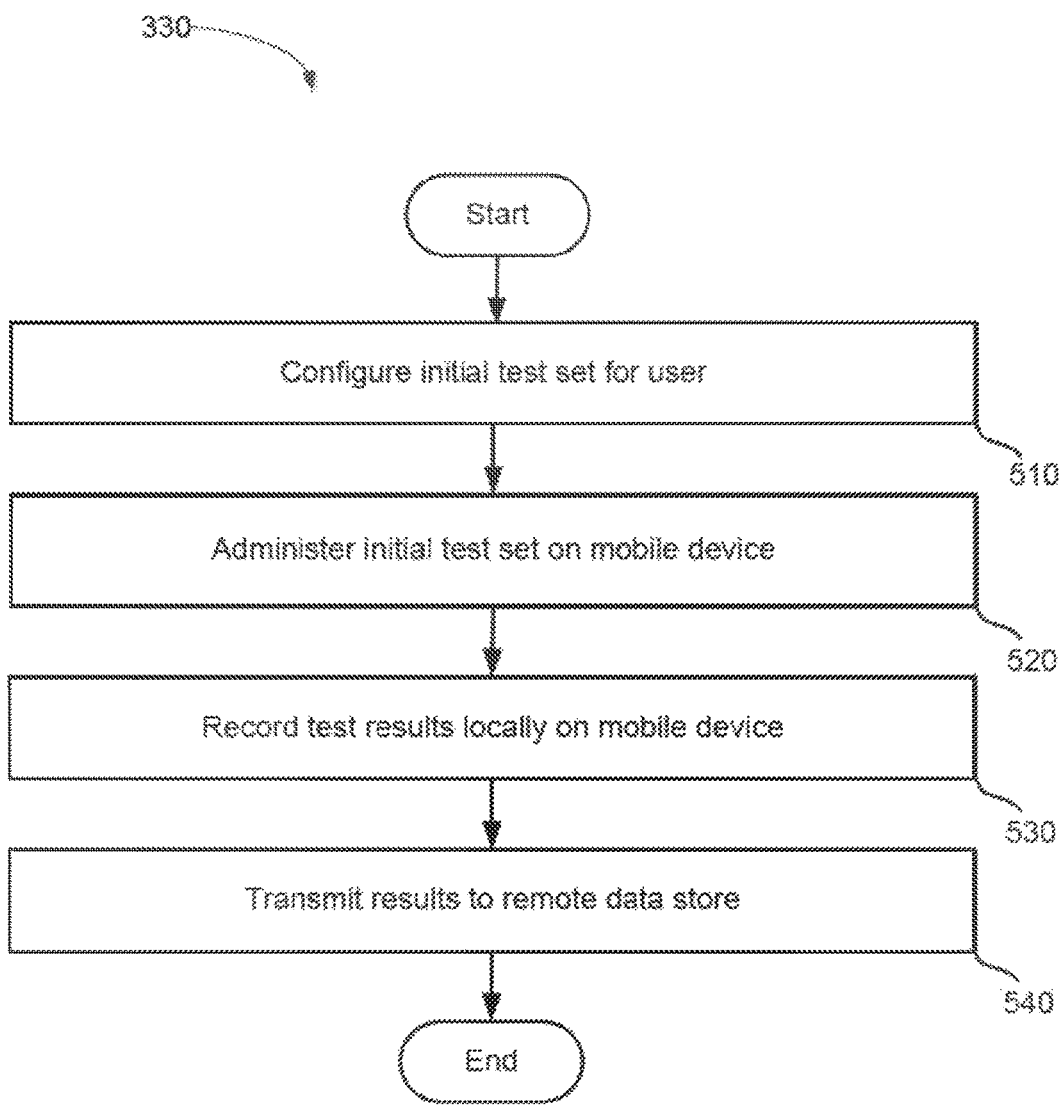
FIG. 5A is a flow chart of a method for administering an initial test set.

FIG. 5A is a flow chart of a method for administering an initial test set. The method of FIG. 5A provides more detail for step 330 of the method of FIG. 2 and may be performed by mobile application 112. An initial test set is configured for a user at step 510. The initial test set may be configured based on user input, user stored data (including age, sex, previous test results and past diagnosis data), physician input, and other data. The initial test set may include tests required to be taken by the user and optional for the user.

The initial test set is administered to the user on the mobile device 110 at step 520. The tests may be administered via one or more interfaces provided through the mobile device 110. Exemplary tests to administer to the user are discussed below with respect to FIGS. 12-19.

Test results from the administered test set are recorded locally at the mobile device at step 530. The test results may be used to configure subsequent tests in the test set and to provide information for a physician to analyze trends and other information. The test results are then transmitted to data store 180 via network 150, network server 160, application server 170 and data store 180. Data store 180 receives the test results and stores the data results as part of the account data associated with the user who was tested.

Figure 5B:
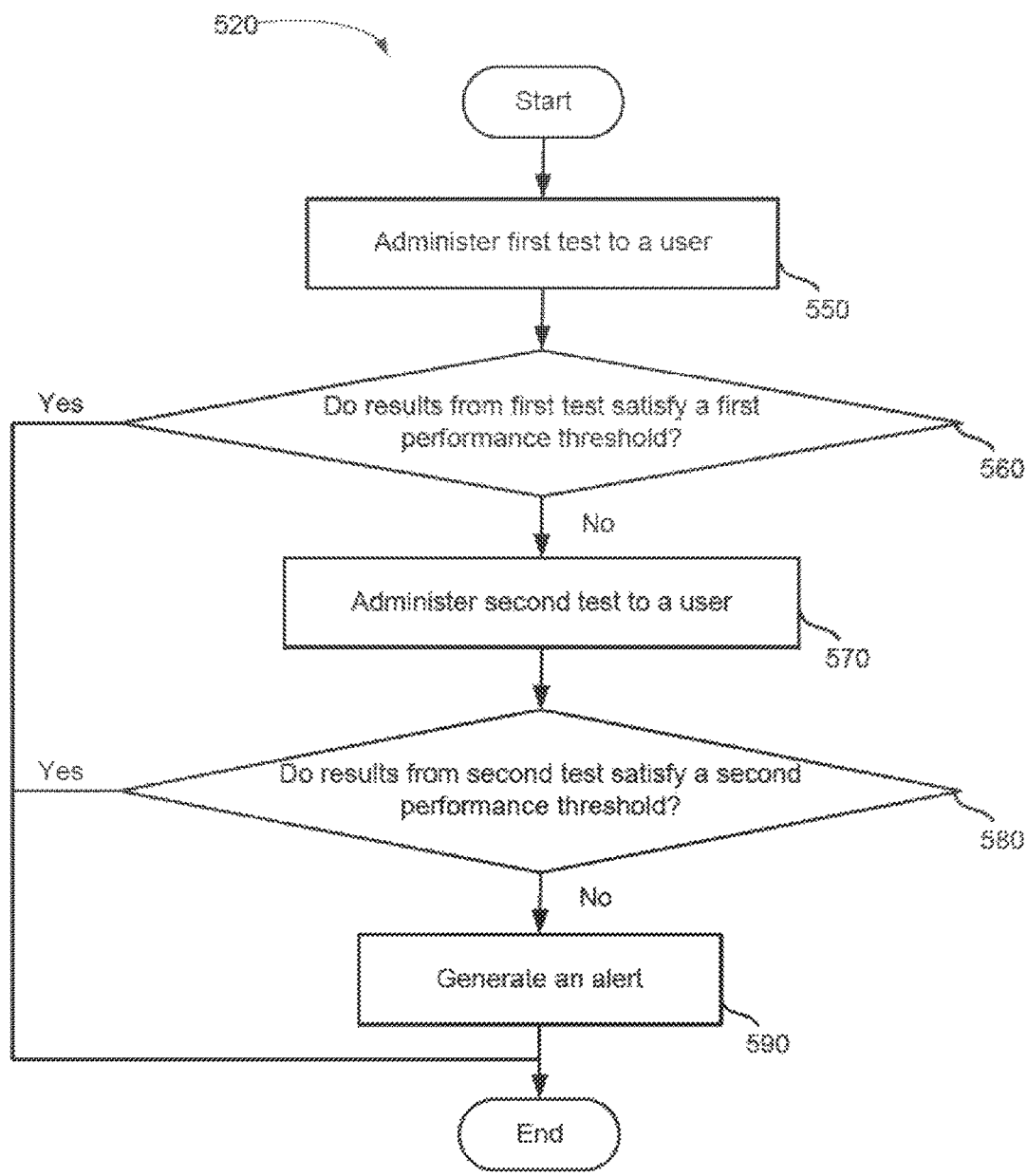
FIG. 5B is a flow chart of a method for administering an initial test set on a mobile device.

FIG. 5B is a flow chart of a method for administering an initial test set on a mobile device. The method of FIG. 5B provides more detail for step 520 of the method of FIG. 5A and may be performed by mobile application 112. A first test is administered to a user at step 550. For example, the first test may be a visual acuity test. A first test may be administered based on a series of difficulty levels. Each difficulty level may be tested through an interface more than once. In various embodiments, a determination is made at step 560 as to whether the results from the first test satisfy a first performance threshold. The first performance threshold may be set by the physician. If the test results satisfy a first performance threshold, the test ends. If the test results do not satisfy a first performance threshold, a second test may be administered to the user.

In various embodiments, no determination occurs at step 560. After administering a first test to a user at step 550, a second test is administered to the user at step 570. The second test may be set at a difficulty level based on the responses, score, level of difficulty, or other parameter from the first test. For example, the difficulty level of the second test may be initially set to the difficulty level in the first test at which two or more correct answers were received.

A second test is administered to the user at step 570. For example, the second test may be a contrast sensitivity test or a color visual acuity test. A determination is made at step 580 as to whether the results from the second test satisfy a second performance threshold. The second performance threshold also may be set by the physician. If the test results satisfy a second performance threshold, the test ends. If the test results do not satisfy a second performance threshold, an alert may be generated at step 590. The alert may be generated for the physician or the user. The alert may include the test result or a recommended action.

The tests administered in a test set may depend on performance in previous tests within the test set. For example, the second test may be administered if user performance in the first test does not satisfy a performance threshold.

In various embodiments, performance in a prior test affects a configuration of a subsequent test. The level of difficulty or other features of the second test may be determined by the results of the first test. For example, the contrast sensitivity test may be administered using fonts sized just above the minimum size that a person could reliably detect in the test of visual acuity. In various embodiments, the setting for a test, such as a level of contrast, sensitivity, font size and screen brightness, may be selected to begin the test at a level close to the typical levels characteristic to the current user. The current user's typical level may be based on previous test performance such as the score from a previous test. This helps to decrease the number of steps necessary to finish the test. Information about the starting point of the test may be extracted from the previous results and analyzed on the mobile device or on a server.

Although the test set or evaluation discussed with reference to FIG. 5B included two tests, a test set may include any number of visual tests. In various embodiments, the test set may be a standard battery of tests administered to all users. In various embodiments, the test set may be a dynamic battery of tests configured for a particular user. In some embodiments a single visual function test is administered.

Figure 6:
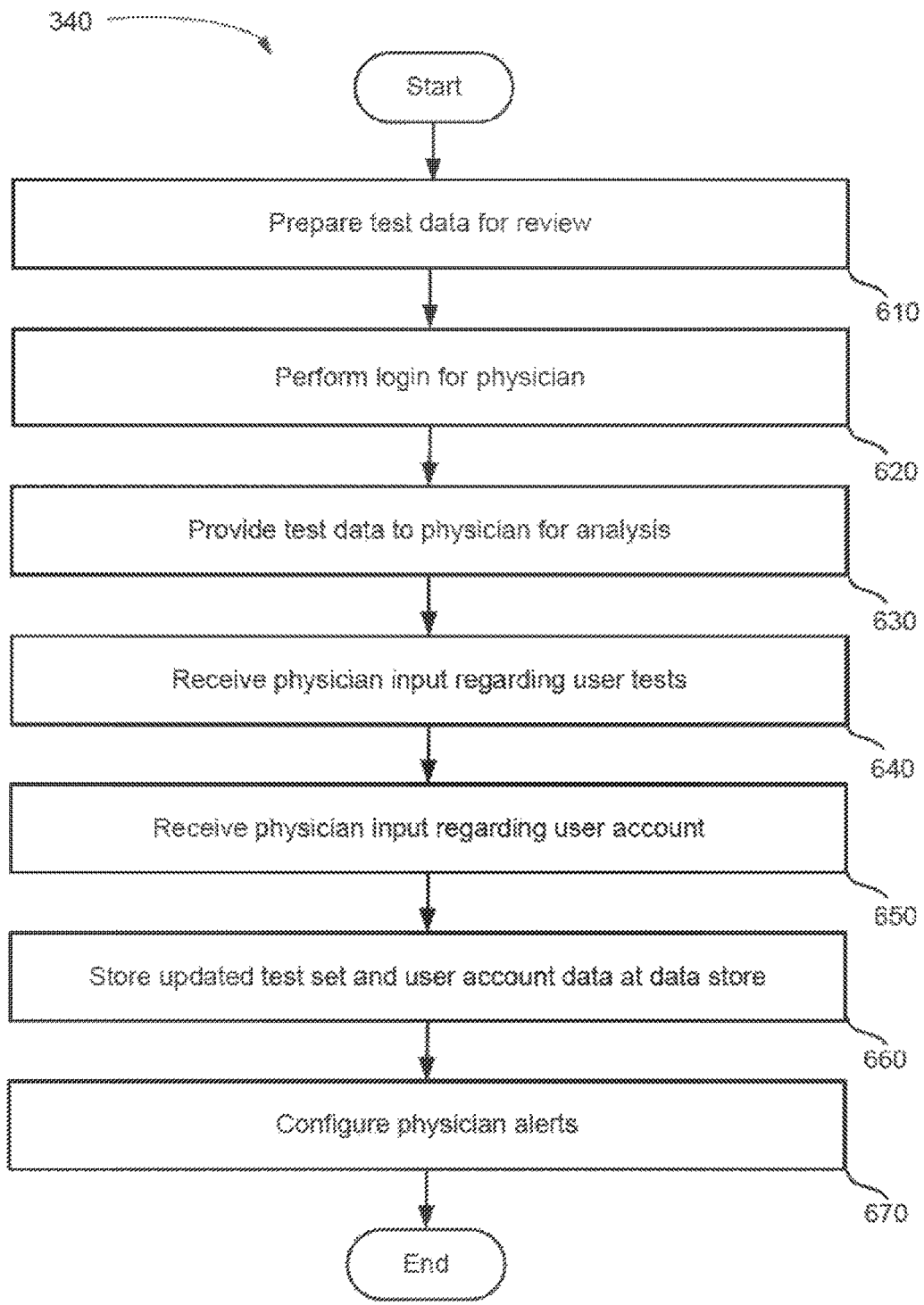
FIG. 6 is a flow chart of a method for analyzing initial test set results.

FIG. 6 is a flow chart of a method for analyzing initial test set results. The method of FIG. 6 provides more detail for step 340 and may be performed by server application 172. Test data is prepared for review at step 610. In some embodiments, test results for a user over time are analyzed for trends. Trends may be identified as normal, improving or a cause for concern. Preparing the test data may include identifying trends and determining if the trends indicate anything that should be of concern.

A physician may login to the network service at step 620. Login for a physician may be similar to user login at step 420 of FIG. 4, except that the physician may login from computer device 130 and may enter physician account information rather than user account information. Physician account information may include business information, alert configuration data, and other data.

Test data is provided to the physician for review at step 630. The physician may review the prepared test data at computer 130. Reviewing test data may include viewing trends of test data, determining whether previous treatments have been successful, and identifying any areas of concern for the user (patient) based on the test data. The results of the analysis may be used by the physician to monitor the user's visual function as a state of a user's current vision-related disease.

Physician input regarding the user tests may be received at step 640. The physician input may be used to reconfigure the test set. The test set may be reconfigured to adjust, add, and remove tests from a test set for the user in view of the trends, treatment response, and areas of concern. Physician input regarding the user account may be received at step 650. The user account input may include a message to the user regarding one or more tests, a request for the user to make an appointment, and adding, deleting, or changing a prescription, or other account information addition, deletion or change. The updated test set and user account data may be stored at data store 180 at step 660.

Alert configuration information may be received from a physician at step 670. The alert configuration information may specify what alerts to set for each user the physician is working with, how the alert is triggered, and an action to take upon each alert. For example, for a particular user, a physician may configure an alert to be triggered upon detecting that the user's vision has degenerated by two or three lines of visual acuity, or a certain percentage of contrast sensitivity in a recent month or other defined period of time. The physician may set the alert action to show up next to patient's name in on the doctor's list of patients, or as an email to the physician. Physician and patient can also be alerted if the patient did not take tests for a certain period of time, or if he missed a scheduled appointment.

Figure 7:
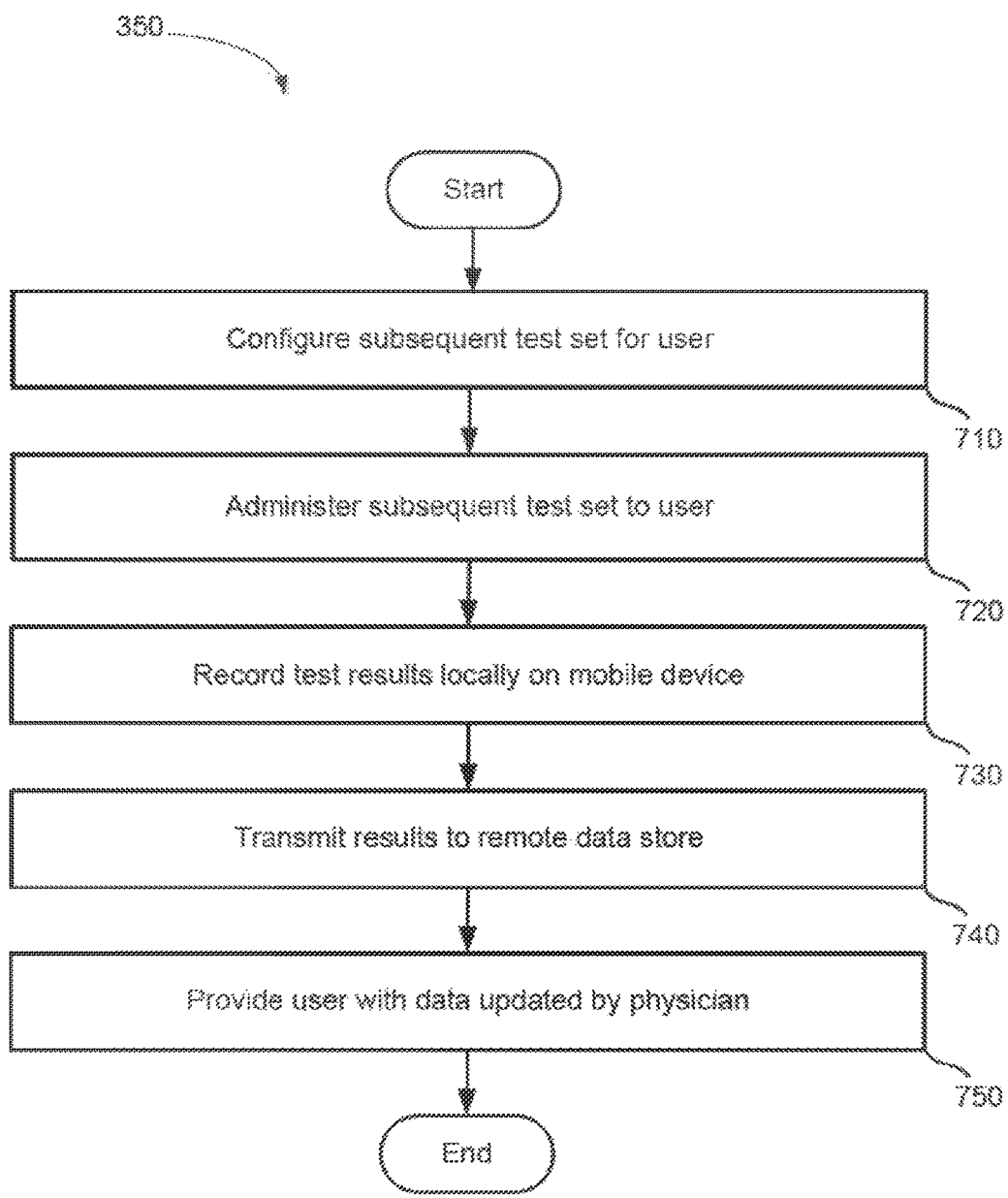
FIG. 7 is a flow chart of a method for configuring subsequent test sets.

FIG. 7 is a flow chart of a method for configuring subsequent test sets. A subsequent test set is configured for a set of users at step 710. The subsequent test set may be configured by the test manager module on mobile application 112. The subsequent test set may be administered to the user at step 720. Test administrator module on mobile application 112 may administer the application to the user through mobile device 112.

Test results from the administered test set are stored locally on mobile device 112 at step 730. The test results may be transmitted to data store 180 at step 740. Data updated by a physician is provided to a user at step 750. The updated data may include changes in account information, such as a physician message regarding a previous test, a request for an appointment, or other information.

The steps of the methods for FIGS. 3-7 are in an exemplary order and not intended to be limiting. The methods of FIGS. 3-7 may be performed at least in part by mobile application 112 and server application 172, as well as by client computers 120-140 used by a user, a physician and a third party.

Figure 8A:
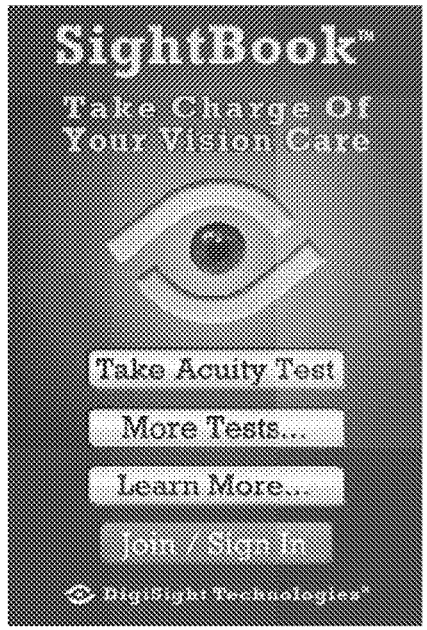
FIGS. 8A-8D illustrate screenshots of an interface for configuring mobile application settings.
Figure 8B:
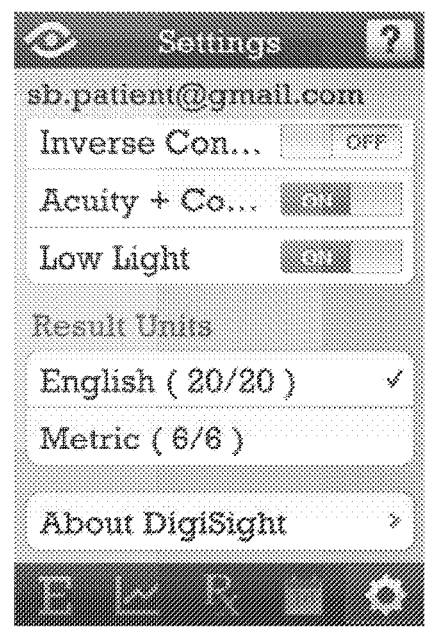
Figure 8C:
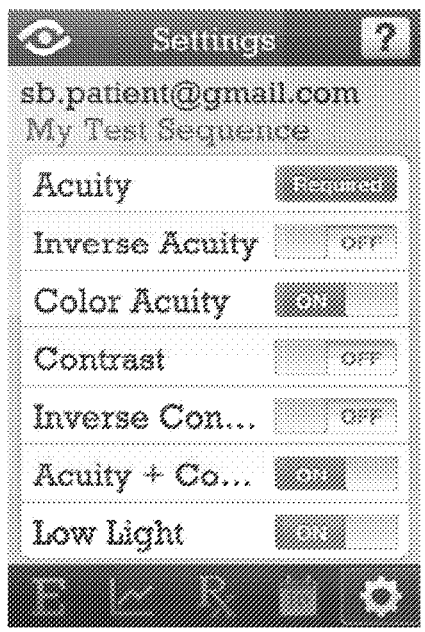
Figure 8D:
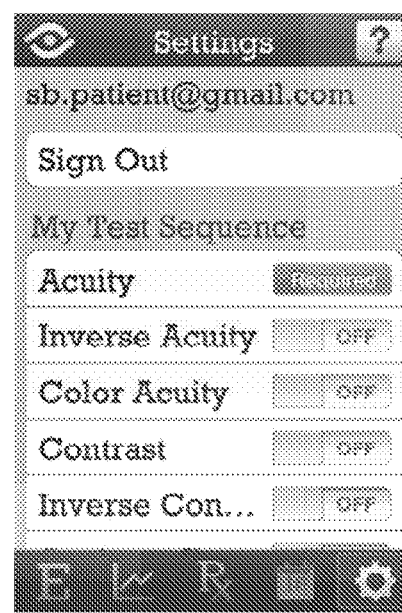

FIGS. 8A-8D illustrate screenshots of an interface for configuring mobile application settings. FIG. 8A illustrates an initial screen for taking tests and joining or logging into the visual function analysis network service. The interface of FIG. 8A receives input selecting an acuity test, more tests, more information, or user login. The interface of FIG. 8B illustrates an interface for receiving settings for particular tests. The interface of FIG. 8B is an interface that receives input for setting each of an inverse contrast, a combination visual acuity and contrast sensitivity test, and low light test on and off, as well as units for test results. FIG. 8C is an interface that also provides settings for individual tests. In particular, the interface of FIG. 8C provides settings for acuity, inverse acuity, color acuity, contrast, inverse contrast, a combination visual acuity and contrast sensitivity test, and low light test. FIG. 8D is an interface that also allows a user to configure settings for different tests, as well as receiving input for a user to sign-out. FIGS. 8B-8D may be part of the same interface which is accessible by scrolling up and down.

FIGS. 9A-9D illustrate screenshots of an interface for managing treatment data. FIG. 9A is an interface that receives a user selection of a treatment type that the user has received in the past. For example, the treatment type may include, but is not limited to, Avastin, Lucentis, Triamcinolone, Ozurdex, VEGF-TRAP, Visudyne, laser or surgery. The interface of FIG. 9B receives eye treatment data from a user. The interface of FIG. 9C allows a user to specify a date and time of a scheduled appointment. The interface of FIG. 9D allows a user to specify a date and time of an eye treatment received. Icons at the bottom of the interface screen correspond to the following in the interfaces of the mobile application: E corresponds to a test interface, the Graph icon corresponds to a results interface, Rx corresponds to a treatment interface, the Calendar icon corresponds to an appointment scheduling interface, the star icon corresponds to the Settings interface.

Figure 10:
FIG. 10 illustrates a screenshot of an interface for managing appointment data.

FIG. 10 illustrates a screenshot of an interface for managing appointment data. The interface of FIG. 10 allows a user to edit and add appointments related to visual testing and treatments, for example with a physician.

FIGS. 11A-11D illustrate screenshots of an interface for managing test data. FIG. 11A illustrates an interface for managing tests for a user. The interface of FIG. 11A allows a user to select a particular test to be edited or configured from a test menu. The interface of FIG. 11B provides additional tests to be edited by a user, and may be part of the same interface illustrated in FIG. 11A. The interface of FIG. 11B also illustrates a "My Test Sequence" which, when selected, provides information for the user's test sequence which can be edited. In various embodiments, the "My Test Sequence" may include a test set selected by the physician.

FIG. 11C provides information for each test taken by a user. For example, the interface of FIG. 11C indicates that a user last took an acuity test on Sep. 22, 2011, but has never taken an inverse contrast test. FIG. 11D provides more detail for an acuity test. The additional information for the acuity test may include previous test dates and results for the user's right eye and left eye.

The visual function evaluation can include a visual acuity test. Table 1 illustrates visual acuity levels for different standards. The visual acuity test can begin with a letter size in the middle of the range, for example 20/70, and decreases by one step or level after each correct response. The test difficulty can increase by one step or level after an incorrect response. The visual acuity test can stop at a level where two or more correct responses have been obtained and with two or more incorrect responses obtained at a level one level harder than the level where the correct responses were obtained. The test can also end when the minimum font size (e.g. 20/20) has been identified correctly two or more times or the maximum font size (e.g. 20/400) has not been answered correctly two or more times. In the latter case the result is ≤20/400.

TABLE 1

| Visual acuity levels | | | | |
|---|---|---|---|---|
| English | Metric | Decimal | LogMAR | ETDRS Letters |
| 20/400 | 6/120 | 0.05 | 1.30 | 20 |
| 20/200 | 6/60 | 0.10 | 1.00 | 35 |
| 20/100 | 6/30 | 0.20 | 0.70 | 50 |
| 20/70 | 6/21 | 0.29 | 0.54 | 58 |
| 20/60 | 6/18 | 0.33 | 0.48 | 61 |
| 20/50 | 6/15 | 0.40 | 0.40 | 65 |
| 20/40 | 2/12 | 0.50 | 0.30 | 70 |
| 20/30 | 6/9 | 0.67 | 0.18 | 76 |
| 20/25 | 6/7.5 | 0.80 | 0.10 | 80 |
| 20/20 | 6/6 | 1.00 | 0.00 | 85 |

Figure 12A:
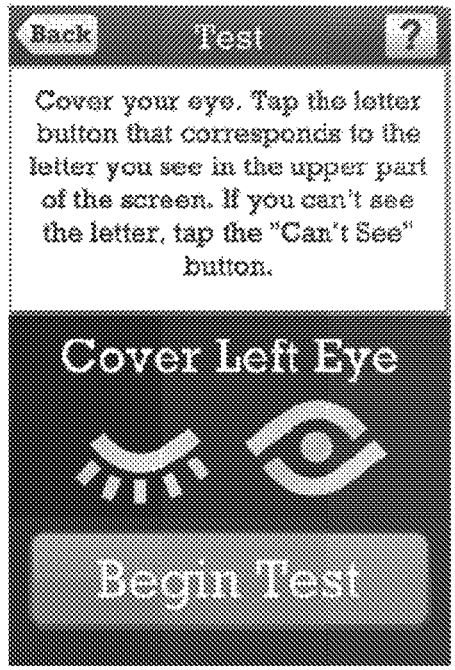
FIGS. 12A-12D illustrate screenshots of an interface for performing a visual acuity test.
Figure 12B:
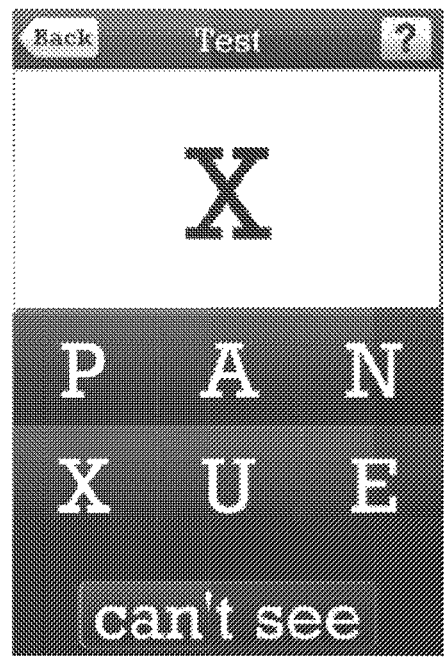
Figure 12C:
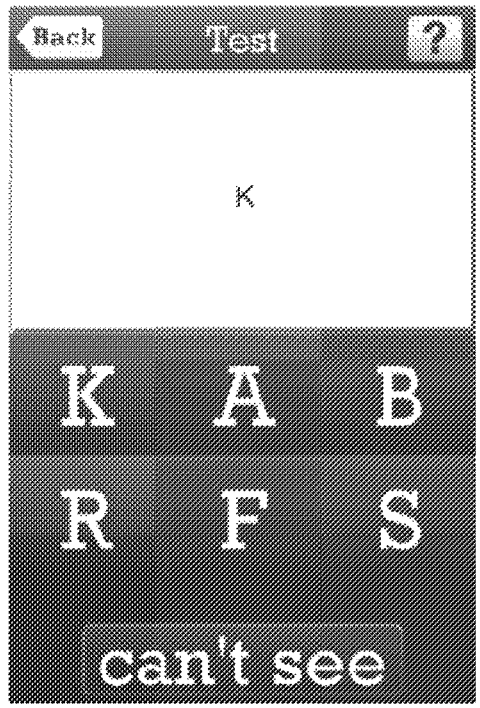
Figure 12D:
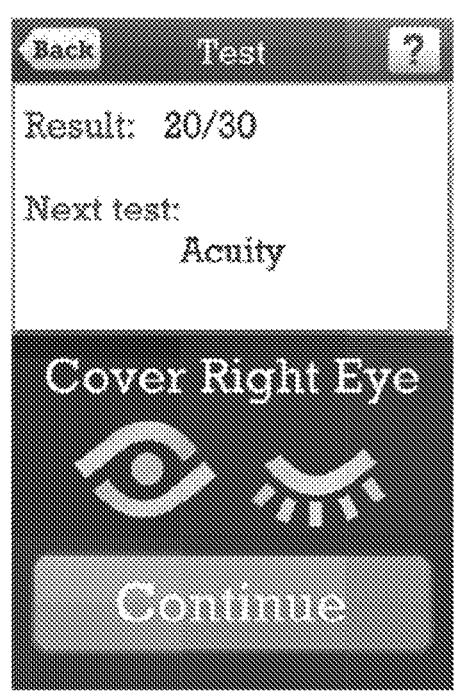
Figure 13A:
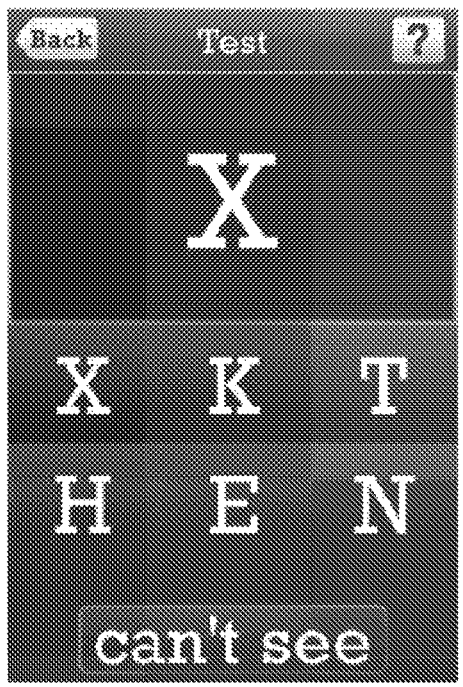
FIGS. 13A-13C illustrate screenshots of an interface for performing an inverse acuity test.
Figure 13B:
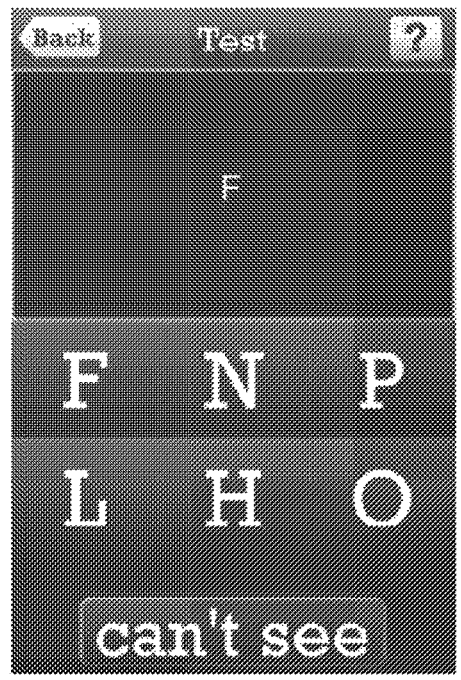
Figure 13C:

FIGS. 12A-12D illustrate screenshots of an interface for performing a visual acuity test. The user interface of FIG. 12A provides a user with instructions before beginning a portion of the visual acuity test for the right eye. The user interface of FIG. 12B provides a user with a test symbol of a particular size and a list of symbols to choose from. The test interface allows a user to select a symbol that the user believes matches the test symbol. Within the interface of FIG. 12B, a letter appears in the test field, and six choices of the letters are shown below it. There is also a button at the bottom "can't see." During the test, the patient provides input to select (e.g., by selection on a touch screen) one of the six letters displayed in the panel below the test window that corresponds to the one displayed in the test field. If the patient touches the correct letter, the next letter will appear smaller. FIG. 12C provides an interface that displays a smaller test symbol and a set of choices for the user to select a symbol which matches the test symbol. If the response is incorrect, or the patient selects the "can't see" button, the letter in the test field becomes larger. The test can end when the patient correctly identifies the smallest font (e.g. 20/20 acuity) or enters a specified number of incorrect responses at a certain level. The healthcare provider can specify the number of incorrect responses. In some embodiments the specified number of incorrect responses is two. In some embodiments the specified number of incorrect responses can be set at three, four, or any higher integer. After the first incorrect answer, the letter becomes larger, if the response indicates correct identification, the letter becomes smaller again. If another incorrect response is determined again at that level, the test ends, and visual acuity will be the lowest level which was correctly identified twice. Alternative choice letters randomly change for every test letter. Letter size is adjusted automatically based on success of the responses, and the result is stored upon completion of the test. FIGS. 13A-13C illustrate screenshots of an interface for performing an inverse acuity test. This test is similar to the visual acuity test only a white letter is displayed on black background of the test window. As the test progresses, the size of the dark letter decreases against a white background, i.e. the test letter becomes progressively smaller. Similar to the visual acuity test, alternative choice letters are randomly changed for every test letter. The letter size may be adjusted automatically based on the success of the responses. The interface of FIG. 13A provides a larger symbol with six symbols for the user to select as a matching symbol, FIG. 13B provides a smaller symbol with six potential matching symbols for selection, and FIG. 13C provides results for the inverse acuity test and instructions for performing the next test.

A low light acuity test can be administered to the patient. For the low light visual acuity test, the interface may initially provide a black letter on a lighter background. In this case the visual acuity is measured first at high contrast. The brightness of the background can then be decreased to 25% and acuity is measured again, starting 2 lines or levels above the acuity level measured at high contrast.

The visual function evaluation can include a contrast sensitivity test. Contrast of the letters in the contrast sensitivity test can be varied according to the Peli-Robson Contrast scale with each step in the contrast sensitivity test. For example, the level of black in the grey can be decreased by approximately $\sqrt{2}$ for each successive step. The level of black in the grey can be digitized according to the LCD screen brightness levels. Therefore the contrast C after N successive steps is calculated as following:

$$= 100 * 2^{\frac{1-n}{2}} (\%).$$

The contrast in this test ranges from 100%, which corresponds to black letters on a white background to 1.1%, which corresponds to very faint grey letters on white background. For example, the calculated contrast for successive steps could be 100%, 70.7%, 50%, 35.4%, 25%, 17.7%, 12.5%, 8.8%, 6.3%, 4.4%, 3.1%, 2.2%, 1.6%, and 1.1%.

The contrast sensitivity test can be configured to begin at a contrast level in the middle of the contrast range, for example at about 25% contrast. The contrast can decrease after each correct response or increases after an incorrect response. The test can end at the level where two or more correct responses have been obtained with two or more incorrect responses obtained at one level harder. Alternatively, the test can end when the minimum contrast (e.g. about 1.1%, has been identified correctly two or more times or the maximum contrast (100%) has not been identified correctly two or more times.

Figure 14A:
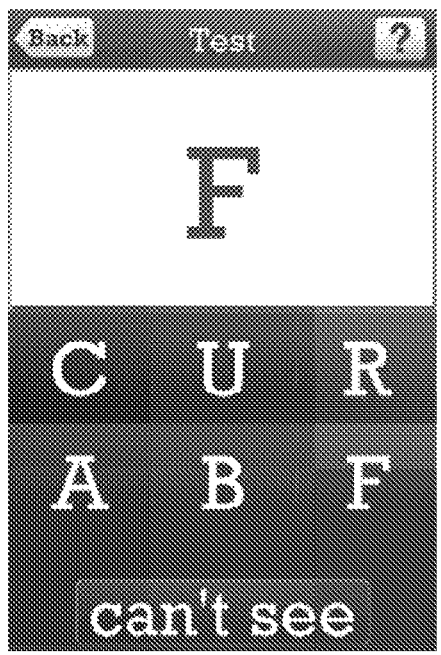
FIGS. 14A-14D illustrate screenshots of an interface for performing a contrast sensitivity test.
Figure 14B:
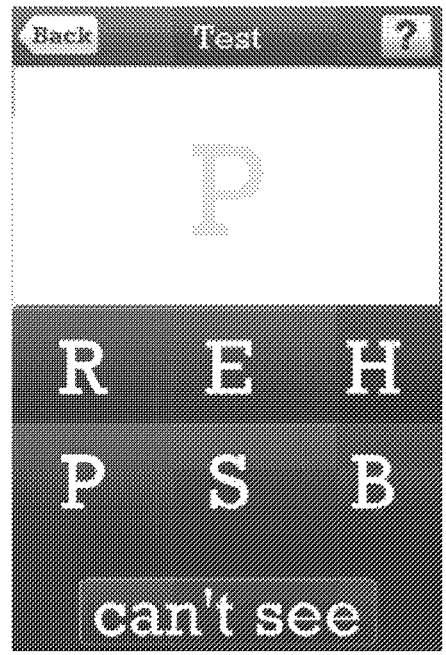
Figure 14C:
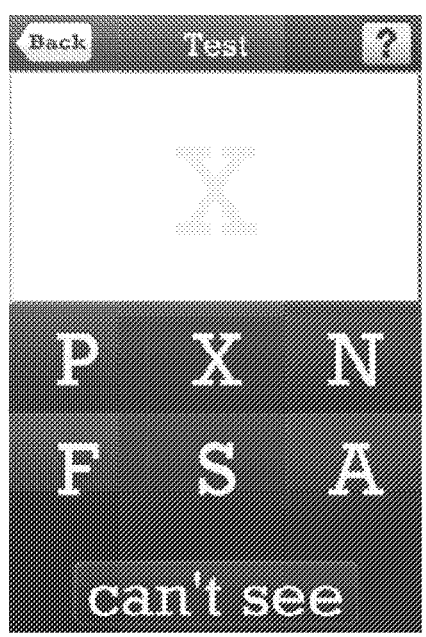
Figure 14D:
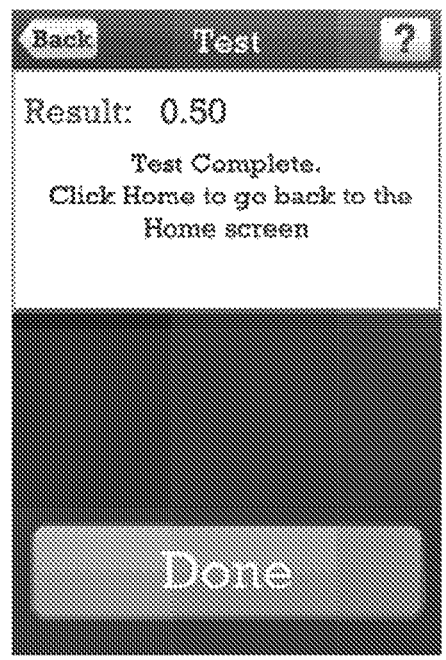
Figure 15A:
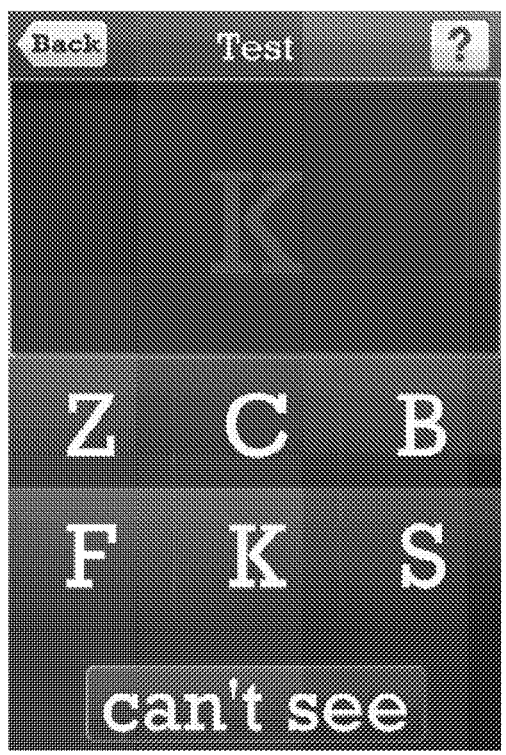
FIGS. 15A-15B illustrate screenshots of an interface for performing a reverse contrast test.
Figure 15B:
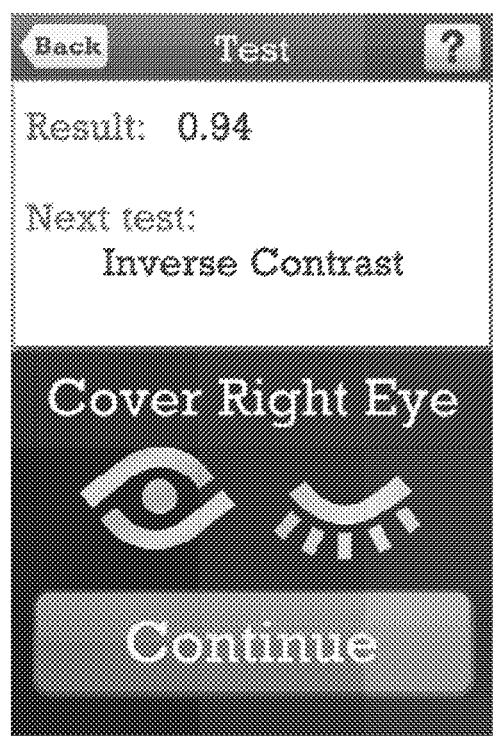

FIGS. 14A-14D illustrate screenshots of an interface for performing a contrast sensitivity test. In the contrast sensitivity test, the symbols become progressively lighter in comparison with the background. The interface of FIG. 14A provides an "F" with a first contrast level along with six potentially matching letter options and a "can't see" button. The interface of FIG. 14B provides a "P" at second contrast level (a lower contrast level) in the test window along with the six potentially matching letter options and a "can't see" button. The interface of FIG. 14C provides an "X" at a third contrast level (lower than the second contrast level) in the test window along with the six potentially matching letter options and a "can't see" button. If the patient selects the correct letter, the contrast decreases. If the patient has an incorrect response or selects the "can't see" button, the contrast will increase. The test ends when a patient has an incorrect response at a certain level of contrast two or more times. FIG. 14C illustrates an interface which provides contrast sensitivity test results to the user. FIGS. 15A-15B illustrate screenshots of an interface for performing an inverse contrast test. The inverse contrast test is similar to the contrast sensitivity test provided through the interfaces of FIGS. 14A-14D, except the test letter is light and the background of the test window is black. During the test, the test letter becomes progressively darker. If the response is correct, the test letter darkens. If the response is incorrect, or the patient selects the "can't see" button, the test letter becomes lighter. The test ends when the patient either correctly identifies the darkest letter, or has an incorrect response at a certain level two or more times. The interface of FIG. 15A provides a "K" against a black background along with six potentially matching letter options and a "can't see" button. FIG. 15B illustrates an interface which provides inverse contrast sensitivity test results to the user.

Figure 16A:
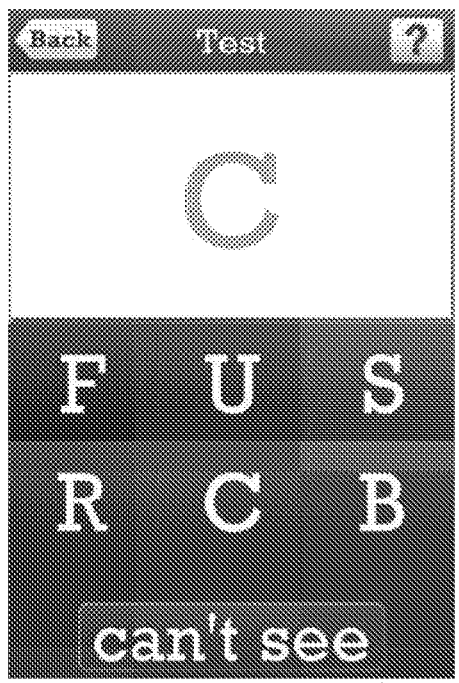
FIGS. 16A-16C illustrate screenshots of an interface for performing a combination visual acuity and contrast sensitivity test.
Figure 16B:
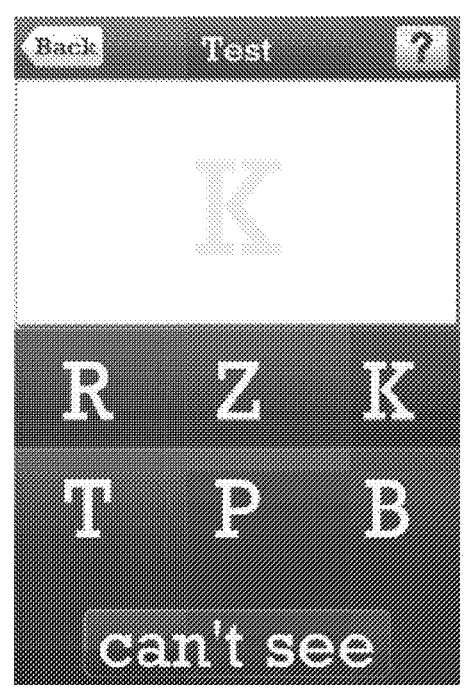
Figure 16C:
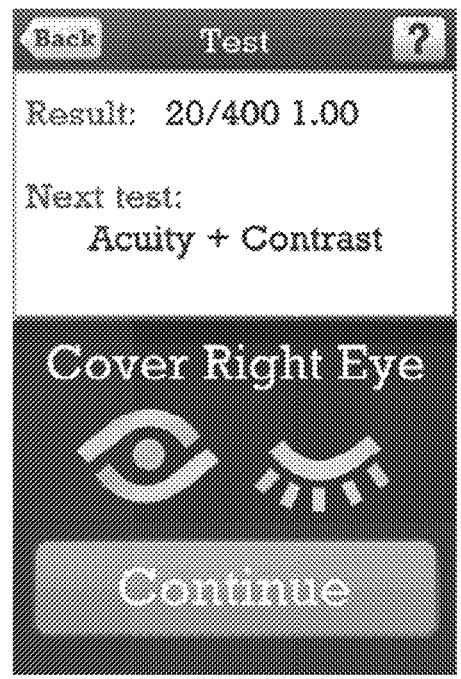

FIGS. 16A-16C illustrates screenshots of an interface for performing a combination visual acuity and contrast sensitivity test. The test begins with a standard test of visual acuity performed with a black letter on white background. After the patient reaches a minimum level, the font size increases by at least one font size number. In various embodiments, the physician selects the appropriate number of sizes to increase the font size and may include one or two font sizes. After the level of acuity is determined from the visual acuity test, the contrast of the letter may start decreasing. The contrast sensitivity test is performed as described with respect to the interfaces of FIGS. 14A-14D. The test ends when the patient either correctly identifies the darkest letter, or has an incorrect response at a certain level twice. This test of contrast sensitivity is more challenging than the same test with large letters, and it is tailored to challenge the patient at their level of visual acuity. As indicated, FIGS. 16A-16B provide interfaces which display letters against a white background. FIG. 16C provides results for the combination test as well as instructions to perform the next test.

Figure 17A:
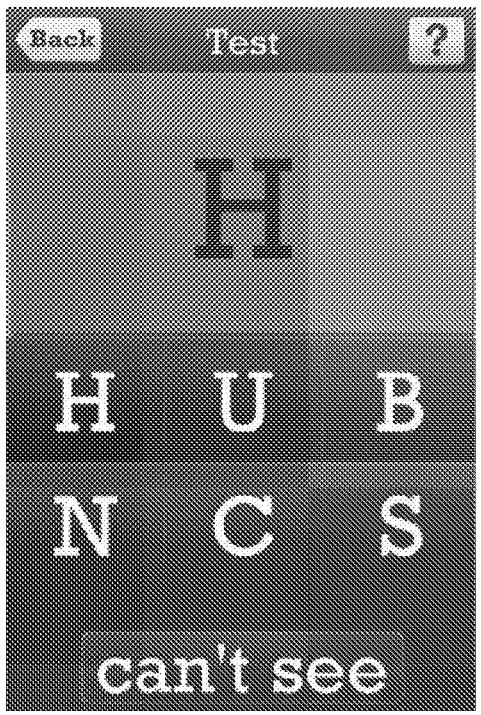
FIGS. 17A-17C illustrate screenshots of an interface for performing low light sensitivity test.
Figure 17B:
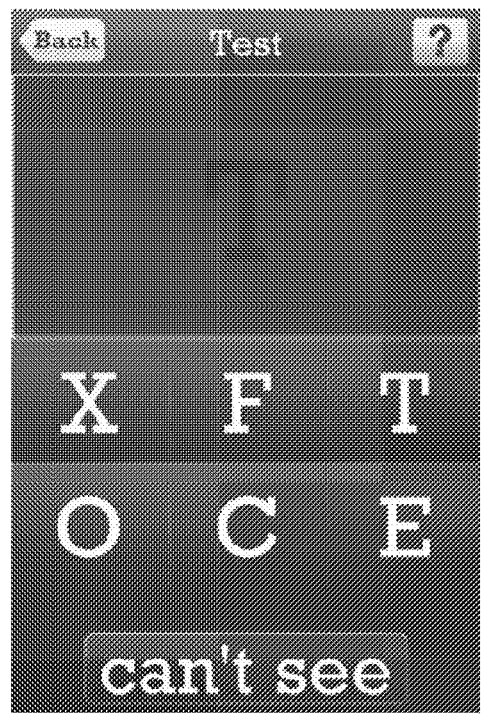
Figure 17C:

FIGS. 17A-17C illustrate screenshots of an interface for performing low light sensitivity test. The low light test mimics the situation with low lighting in a room. For the low light sensitivity test, the interface may initially provide a black letter on white background. The background of the test window gets darker with each correct response, and lighter if the patient selects the "can't see" button or with each incorrect response. The test ends when the patient either correctly identifies the letter with the darkest background, or has an incorrect response at a certain level twice. Alternative choice letters may randomly change for every test letter as in the interfaces for the visual acuity test of FIGS. 12A-12D. FIGS. 17A-17B illustrate interfaces having black letters and progressively darker backgrounds, along with a selection of six potential matching letters and a "can't see" button. The interface of FIG. 17C provides results to a user and instructions for the next test. The contrast sensitivity test can begin at a desired contrast level. For example, a background level of 50% of white can be used for the first step.

Figure 18A:
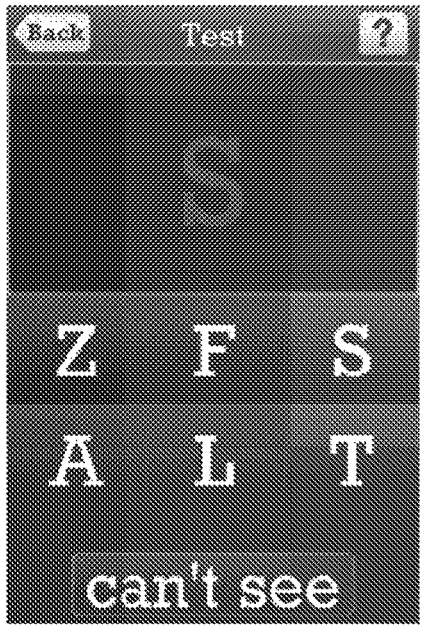
FIGS. 18A-18D illustrate screenshots of an interface for performing a color visual acuity test.
Figure 18B:
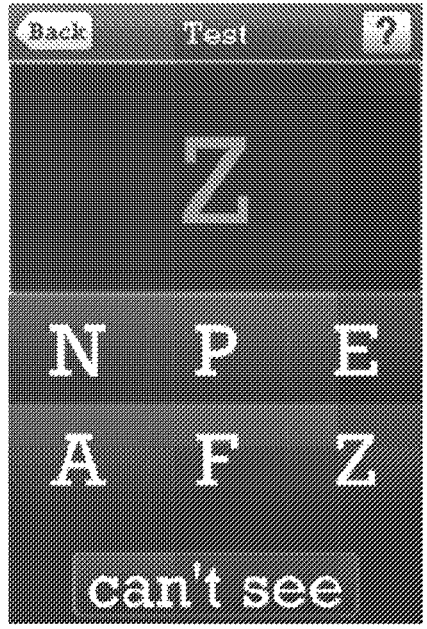
Figure 18C:
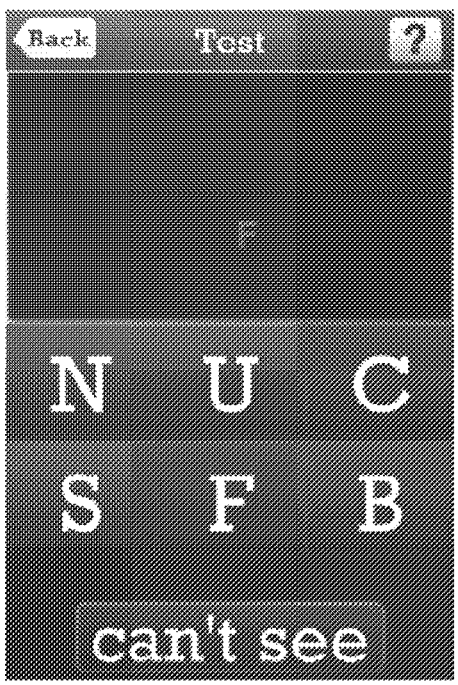
Figure 18D:
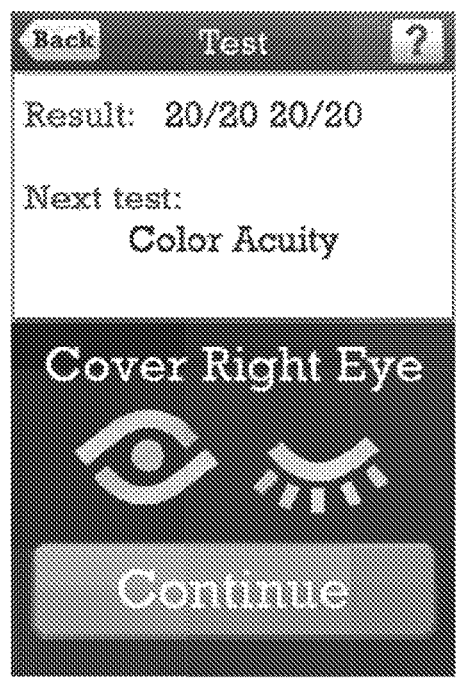

FIGS. 18A-18D illustrate screenshots of an interface for performing a color visual acuity test. The color visual acuity test measures visual acuity with different colored fonts. For example, blue colored fonts may be used for the first part of the test and red colored fonts may be used for the second part of the test. The color of the font may include blue, red, green, yellow or any other color. FIGS. 18A and 18B display a larger blue "S" and red "Z", respectively, along with a selection of six potential matching letter options and a "can't see" button. FIG. 18C displays a smaller letter "F" in blue along with a selection of six potential matching letters and a "can't see" button. The color acuity test is performed in a similar manner as the visual acuity test as described with respect to the interfaces of FIGS. 12A-12D. The interface of FIG. 18D provides results to a user and instructions to perform the next test. Discrepancy between these tests is indicative of either retinal disease or cataract.

Figure 19A:
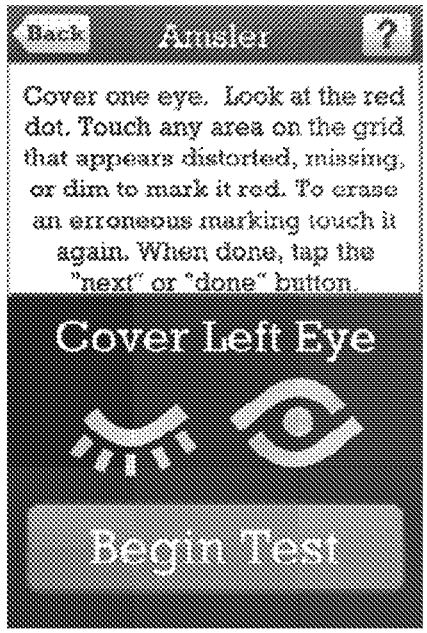
FIGS. 19A-19D illustrate screenshots of an interface for performing an Amsler grid test.
Figure 19B:
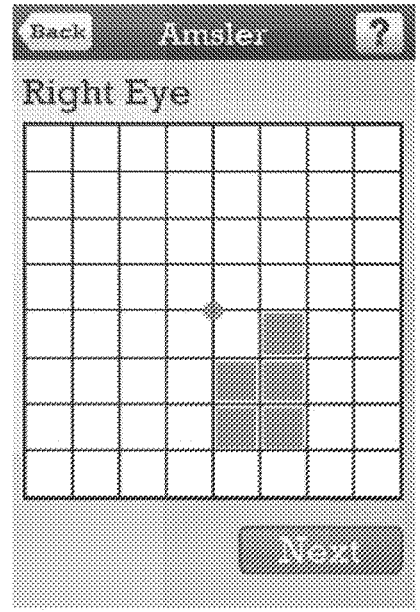
Figure 19C:
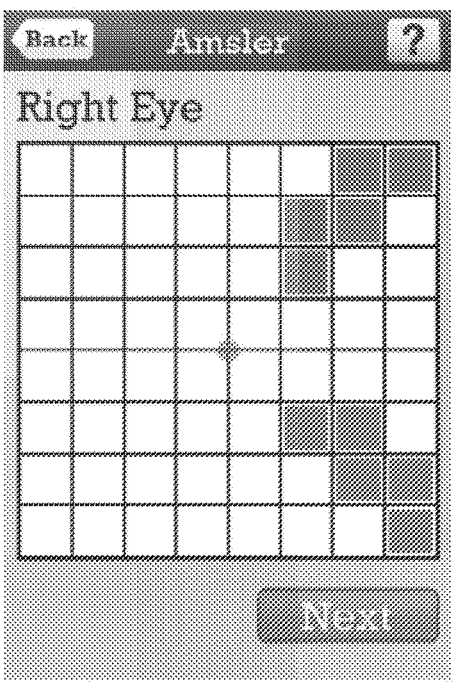
Figure 19D:
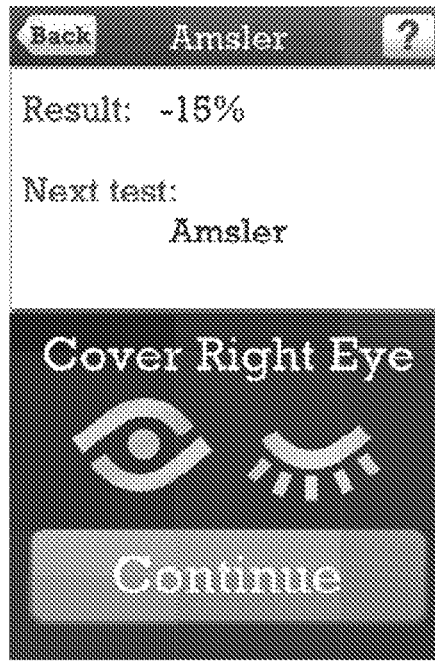

FIGS. 19A-19D illustrate screenshots of an interface for performing an Amsler grid test. The Amsler grid test shows a grid of lines through an interface. The patient is provided an interface with a fixation point in the center of the grid (red point) and prompted to mark the areas that appear distorted. The interface then receives user (patient) input in the areas of image distortion. For example, with a touch screen interface, the patient may touch the screen in the areas where the grid appears distorted. The image distortion may include a reduced contrast, curved lines, and/or missing part of the image. Similar to previous tests described, a correct response increases the level of difficulty and an incorrect response or selection of the "can't see" button decreases the level of difficulty. The test ends when a patient responds incorrectly twice at a certain level. The Amsler grid test detects image distortion and small variations in retinal sensitivity. It may be useful in identifying the earliest symptoms of macular disease. FIG. 19A includes an interface which provides instructions for the user to begin the Amsler grid test. FIGS. 19B-19C provide an interface having a grid of lines with shaded portions to be selected by a user. FIG. 19D provides an interface which displays the results of the Amsler grid test for an eye and prompts the user to continue with the Amsler test for a right eye. Areas marked by the patient through an interface provided by the mobile application may then be quantified in terms of the total surface area and location relative to the fixation center. The quantifying may be performed by the mobile application or remotely by a server application. Distortion can be indicative of a transition from dry macular degeneration disease to wet macular degeneration disease.

The exemplary visual function tests described above with respect to FIGS. 12-19 are not intended to be limiting. In various embodiments, a visual function test includes a test object, letter or shape. The visual function test may vary the test object, letter or shape in any combination including color, contrast (field) or brightness (light/dark). The background of the test window may also vary in any combination of color, contrast (field) or brightness (light/dark). The visual function tests may also be dynamic, such as responding to flashes on the screen (mapping of visual field sensitivity), moving text or changing text (reading speed). The visual function tests may also include "undoing" the distortion in the field by shifting lines to make them appear straight. Generally speaking, correct responses increase the level of difficulty and incorrect responses decrease the level of difficulty. A visual function test may end when the user errs twice at a certain level of difficulty and provides a correct answer twice at the previous level. Other integers can be used for the number of correct and incorrect responses.

Figure 20A:
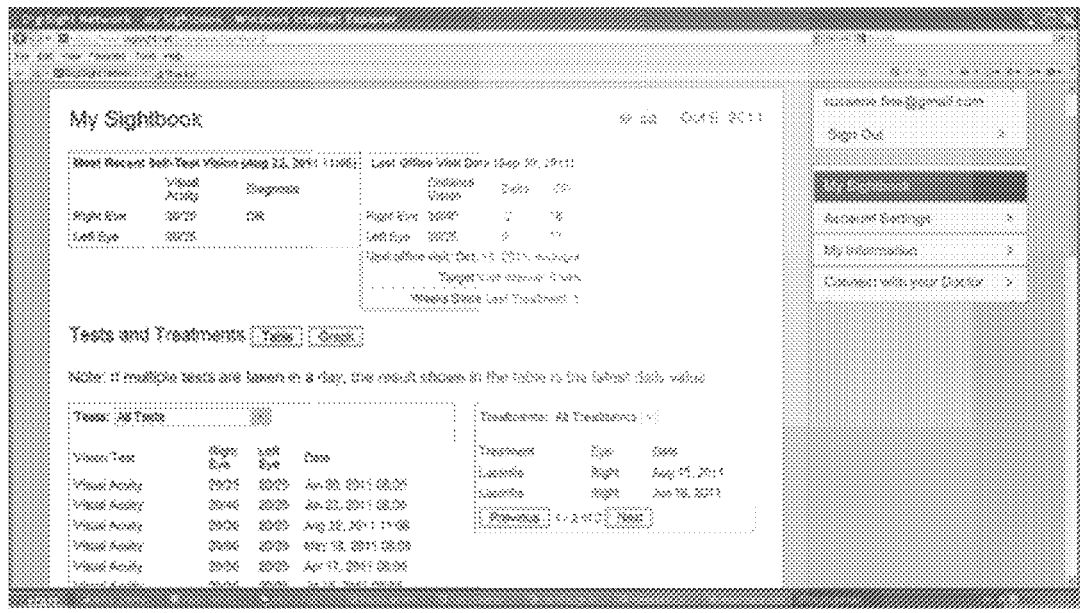
FIGS. 20A-20B illustrate screenshots of an interface of a patient user dashboard.
Figure 20B:

FIGS. 20A-20B illustrate screenshots of an interface of a patient user dashboard. FIG. 20A provides an interface dashboard having information for a user's account with the visual test and analysis service. The dashboard presents data such as the most recent self-test visual function test, the last office visit data, and test and treatment data which may be presented in either table or graph format. Within the user dashboard, a user may select to view their home page ("My Sightbook"), account settings page, My Information page, and request to connect with the user's physician.

Within FIG. 20A, the user can select to view trend data for a particular test. The trend data may be presented in a table format or as a graphical representation. The interface of FIG. 20B provides a graphical representation of trend data for a visual acuity test for the user's right eye. The trend data plots the user test scores for the test over a period from February 1 to August 1 within a year. The test data and time period may vary based on user input and available data. In various embodiments, the trend data plot my also include when a treatment is received. For example, an "L" indicates when the user (patient) was administered a treatment of Lucentis. The trend data varies for each individual. For example, a first user (patient) may require a pharmacological treatment every four to six weeks while a second user (patient) may require the same pharmacological treatment every six to eight weeks. Monitoring the trend data of each individual user may allow the physician to personalize and manage treatment for each user. In addition, the trend data may better predict when the user is in need of a treatment.

Figure 21:
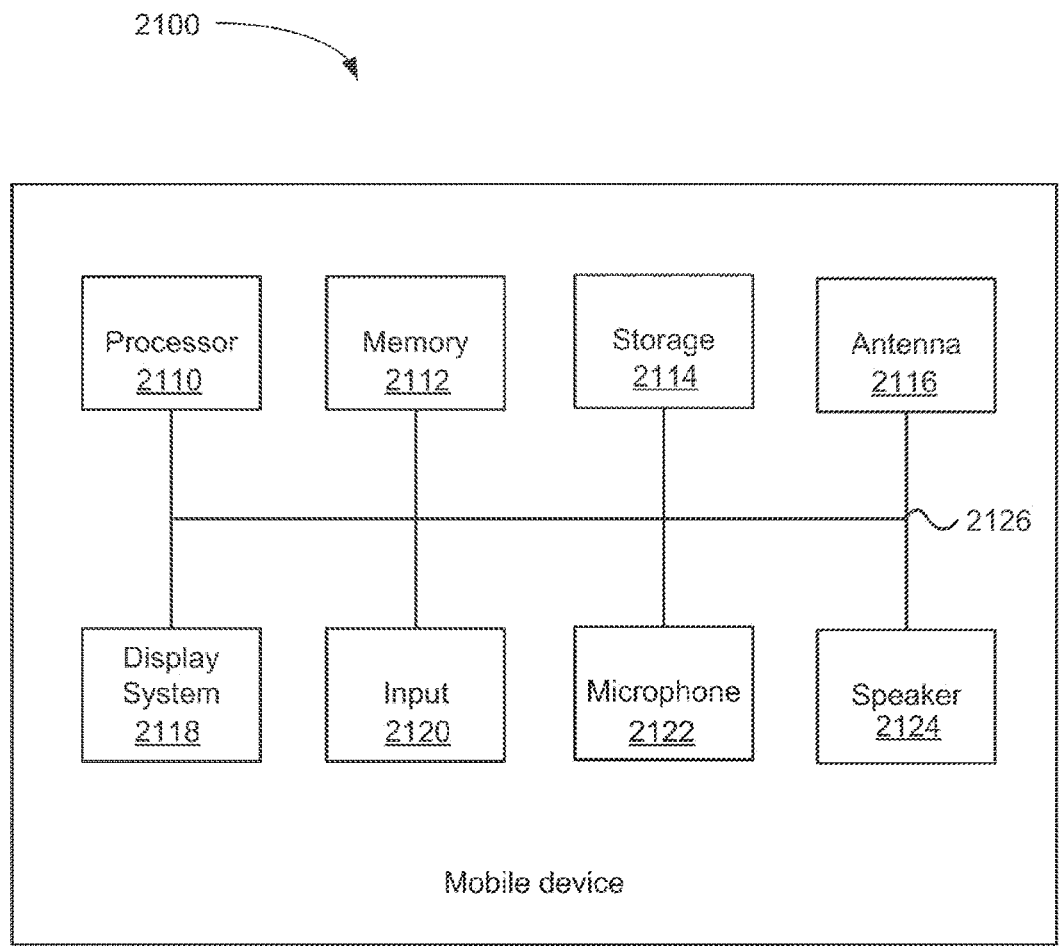
FIG. 21 is a block diagram of an exemplary system for implementing a mobile device.

FIG. 21 illustrates an exemplary mobile device system 2100 that may be used to implement a mobile device for use with the present technology, such as for mobile device 212. The mobile device 2100 of FIG. 21 includes one or more processors 2110 and memory 2112. Memory 2112 stores, in part, programs, instructions and data for execution and processing by processor 2110. The system 2100 of FIG. 21 further includes storage 2114, one or more antennas 2116, a display system 2118, inputs 2120, one or more microphones 2122, and one or more speakers 2124.

The components shown in FIG. 21 are depicted as being connected via a single bus 2126. However, the components 2110-2124 may be connected through one or more data transport means. For example, processor unit 2110 and main memory 2112 may be connected via a local microprocessor bus, and storage 2114, display system 2118, input 2120, and microphone 2122 and speaker 2124 may be connected via one or more input/output (I/O) buses.

Memory 2112 may include local memory such as RAM and ROM, portable memory in the form of an insertable memory card or other attachment (e.g., via universal serial bus), a magnetic disk drive or an optical disk drive, a form of FLASH or PROM memory, or other electronic storage medium. Memory 2112 can store the system software for implementing embodiments of the present invention for purposes of loading that software into main memory 2110.

Antenna 2116 may include one or more antennas for communicating wirelessly with another device. Antenna 2116 may be used, for example, to communicate wirelessly via Wi-Fi, Bluetooth, with a cellular network, or with other wireless protocols and systems. The one or more antennas may be controlled by a processor 2110, which may include a controller, to transmit and receive wireless signals. For example, processor 2110 execute programs stored in memory 2112 to control antenna 2116 transmit a wireless signal to a cellular network and receive a wireless signal from a cellular network.

Display system 2118 may include a liquid crystal display (LCD), a touch screen display, or other suitable display device. Display system 2118 may be controlled to display textual and graphical information and output to text and graphics through a display device. When implemented with a touch screen display, the display system may receive input and transmit the input to processor 2110 and memory 2112.

Input devices 2120 provide a portion of a user interface. Input devices 2160 may include an alpha-numeric keypad, such as a keyboard, for inputting alpha-numeric and other information, buttons or switches, a trackball, stylus, or cursor direction keys.

Microphone 2122 may include one or more microphone devices which transmit captured acoustic signals to processor 2110 and memory 2112. The acoustic signals may be processed to transmit over a network via antenna 2116. Microphone 2122 may receive acoustic signals that can be analyzed by voice recognition software to identify user commands. The user commands can be processed as input to perform different tasks and control the mobile application instead of a touchscreen.

Speaker 2124 may provide an audio output for mobile device 2100. For example, a signal received at antenna 2116 may be processed by a program stored in memory 2112 and executed by processor 2110. The output of the executed program may be provided to speaker 2124 which provides audio. Additionally, processor 2110 may generate an audio signal, for example an audible alert, and output the audible alert through speaker 2124.

The mobile device system 2100 as shown in FIG. 21 may include devices and components in addition to those illustrated in FIG. 21. For example, mobile device system 2100 may include an additional network interface such as a universal serial bus (USB) port.

The components contained in the computer system 2100 of FIG. 21 are those typically found in mobile device systems that may be suitable for use with embodiments of the present invention and are intended to represent a broad category of such mobile device components that are well known in the art. Thus, the computer system 2100 of FIG. 21 can be a cellular phone, smart phone, hand held computing device, minicomputer, or any other computing device. The mobile device can also include different bus configurations, networked platforms, multi-processor platforms, etc. Various operating systems can be used including Unix, Linux, Windows, Macintosh OS, Google OS, Palm OS, and other suitable operating systems.

Figure 22:
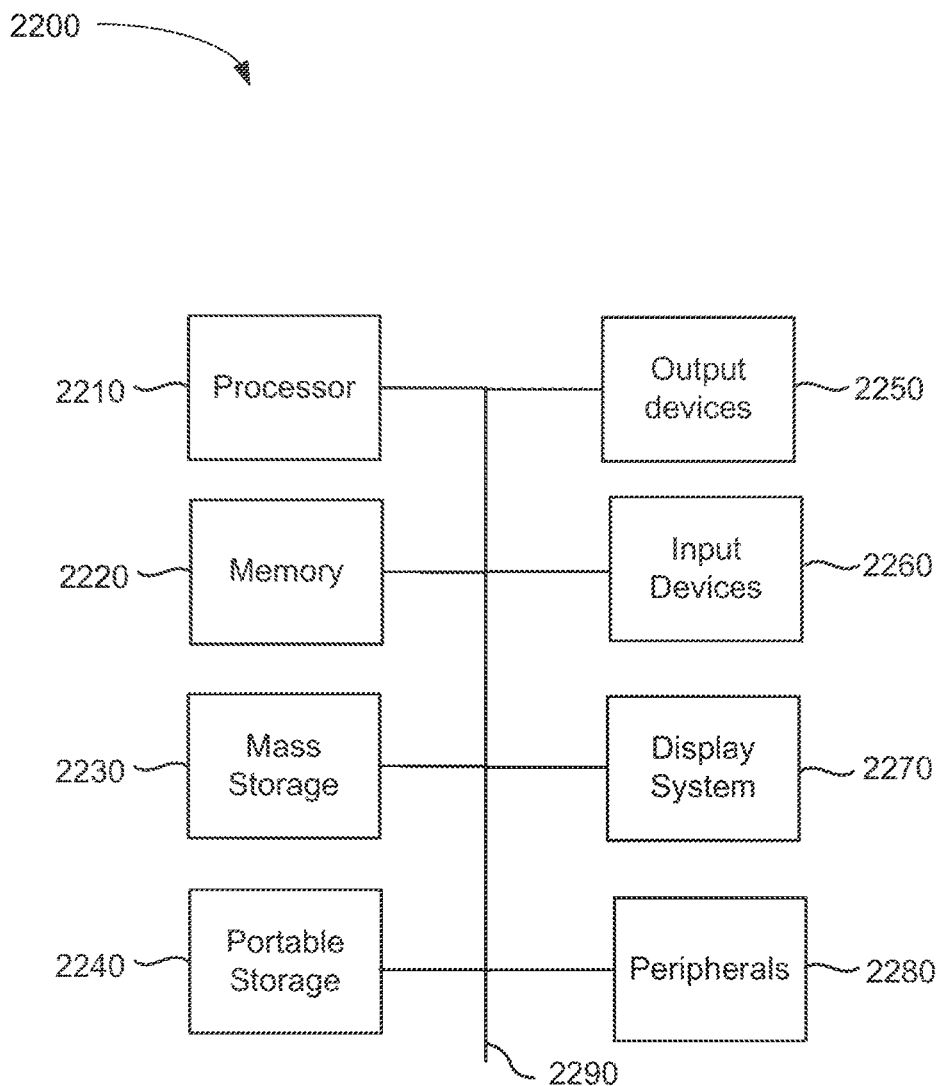
FIG. 22 is a block diagram of an exemplary system for implementing a computing device.

FIG. 22 illustrates an exemplary computing system 2200 that may be used to implement a computing device for use with the present technology. System 2200 of FIG. 22 may be implemented in the contexts of the likes network server 160, application server 170, data store 180, and client devices 120-140. The computing system 2200 of FIG. 22 includes one or more processors 2210 and memory 2220. Main memory 2220 stores, in part, instructions and data for execution by processor 2210. Main memory 2220 can store the executable code when in operation. The system 2200 of FIG. 22 further includes a mass storage device 2230, portable storage medium drive(s) 2240, output devices 2250, user input devices 2260, a graphics display 2270, and peripheral devices 2280.

The components shown in FIG. 22 are depicted as being connected via a single bus 2290. However, the components may be connected through one or more data transport means. For example, processor unit 2210 and main memory 2220 may be connected via a local microprocessor bus, and the mass storage device 2230, peripheral device(s) 2280, portable storage device 2240, and display system 2270 may be connected via one or more input/output (I/O) buses.

Mass storage device 2230, which may be implemented with a magnetic disk drive or an optical disk drive, is a non-volatile storage device for storing data and instructions for use by processor unit 2210. Mass storage device 2230 can store the system software for implementing embodiments of the present invention for purposes of loading that software into main memory 2220.

Portable storage device 2240 operates in conjunction with a portable non-volatile storage medium, such as a floppy disk, compact disk or Digital video disc, to input and output data and code to and from the computer system 2200 of FIG. 22. The system software for implementing embodiments of the present invention may be stored on such a portable medium and input to the computer system 2200 via the portable storage device 2240.

Input devices 2260 provide a portion of a user interface. Input devices 2260 may include an alpha-numeric keypad, such as a keyboard, for inputting alpha-numeric and other information, or a pointing device, such as a mouse, a trackball, stylus, or cursor direction keys. Additionally, the system 2200 as shown in FIG. 22 includes output devices 2250. Examples of suitable output devices include speakers, printers, network interfaces, and monitors.

Display system 2270 may include a liquid crystal display (LCD) or other suitable display device. Display system 2270 receives textual and graphical information, and processes the information for output to the display device.

Peripherals 2280 may include any type of computer support device to add additional functionality to the computer system. For example, peripheral device(s) 2280 may include a modem or a router.

The components contained in the computer system 2200 of FIG. 22 are those typically found in computer systems that may be suitable for use with embodiments of the present invention and are intended to represent a broad category of such computer components that are well known in the art. Thus, the computer system 2200 of FIG. 22 can be a personal computer, hand held computing device, telephone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Palm OS, and other suitable operating systems.

Example 1

A user receiving an intraocular eye injection can use the mobile device application to test visual function. The healthcare provider selects the visual function tests from the list of available test on the mobile device application for the user based on the intraocular eye injection treatment. The test data can be transmitted to the remote computer and tracked between injections. Different users will respond to the injections differently and have different periodicity between treatments. The test data can be analyzed to determine how the user's vision changes between treatments. The analysis can be used to predict when the user should receive the next injection. Tailoring the injection treatment to the specific user improves the efficiency of the treatment for the user.

The test data can also be used to detect a larger than usual decrease in the visual function of the user and provide an alert to the user and healthcare provider that treatment or evaluation by a healthcare provider may be necessary.

Example 2

A user with a dry macular degeneration disease can use the mobile device application to test the user for progression to wet macular degeneration disease. Distortion tests can be used to detect the presence of wet macular degeneration. The healthcare provider can select a distortion test, such as an Amsler grid, for the user. The user can take the distortion test on the mobile device. If the results of the distortion test indicate distortion then an alert can be generated for the user and healthcare provider to signal the need for evaluation of the user's visual function. The treatment programs are different between wet and dry macular degeneration diseases, thus the presence of wet macular degeneration disease can result in a different course of treatment for the user.

Example 3

A user receiving a recurrent treatment can use the mobile device application to test their visual function. The test data is analyzed to determine a baseline level of performance for the user. The healthcare provider sets a delta level for the user. If the user's test data varies from the baseline level of performance by more than the set delta level then an alert is sent to the user and the healthcare provider. The alert can prompt the user's physician to review the visual function test data for the user and determine whether the user should visit to the physician's office for an evaluation. If the physician determines that the user should visit the physician's office a message from the physician can be sent to the user on the user's mobile device. The message can prompt the user to schedule an appointment.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. The present invention descriptions are intended to cover such alternatives, modifications, and equivalents as may be included within the spirit and scope of the invention as defined by the appended claims and otherwise appreciated by one of ordinary skill in the art.

What is claimed is:

1. A method for performing a visual function evaluation of a patient with a retinal disease who is under recurrent treatment, the method comprising:
   executing a patient administered visual function evaluation on a mobile device, wherein the evaluation includes one or more visual function tests pre-selected by a healthcare provider, wherein each test is comprised of a number of steps and the difficulty of a subsequent step is based on a patient's response to a previous step within the test;
   indicating using a touch screen on the mobile device at least one response to a healthcare provider pre-selected test based on a patient specific or a retinal disease specific criteria;
   transmitting the visual function evaluation results and the at least one response to a healthcare provider pre-selected test from the mobile device to a remote server;
   analyzing the results of the visual function evaluation and the at least one response to a healthcare provider pre-selected test using the remote server to determine trends in the patient's visual function based on the most recent results and previous data;
   analyzing the trends to determine if a next treatment is to be scheduled; and
   predicting a time for the next treatment for the patient based on the trends in the patient's visual function.

2. The method of claim 1, wherein the healthcare provider pre-selected test based on the patient specific or the disease specific criteria relates to an assessment for a progression of the retinal disease.

3. The method of claim 1, wherein the recurrent treatment is for a first retinal disease and the healthcare provider pre-selected test based on the patient specific or the disease specific criteria relates to an assessment of the existence of a second retinal disease that is different from the first retinal disease.

4. The method of claim 3 wherein the first retinal disease is dry macular degeneration and the second retinal disease is wet macular degeneration.

5. The method of claim 4 wherein the one or more visual function tests pre-selected by a healthcare provider includes a distortion test.

6. The method of claim 5 the analyzing the result step further comprising generating an alert of the results of the distortion test for evaluation of the patient's visual function.

7. The method of claim 5 the analyzing the result step further comprising generating an alert of the results of the distortion test with a recommendation for a pharmacological treatment or for concurrent monitoring of the disease progression of the first retinal disease and the second retinal disease.

8. The method of claim 4, wherein the analysis of the trends in the patient's visual function compares the trends in the patient's visual function to trends for other patients or groups of other patients who are administered the same pharmacological agent.

9. The method of claim 8, wherein the pharmacological agent is a VEGF inhibitor.

10. The method of claim 9, wherein the VEGF inhibitor is Lucentis or Avastin.

11. The method of claim 8, wherein the pharmacological agent is Triamcinolone, Ozurdex, VEGF-TRAP, or Visudyne.

12. The method of claim 3, the recurrent treatment further comprising: visiting a physician's office and conducting testing under the guidance of a healthcare provider to determine the need for further treatment.

13. The method of claim 1, wherein the test is pre-selected by the healthcare provider based on the recurrent treatment.

14. The method of claim 13, wherein the recurrent treatment comprises monitoring disease progression or administration of a pharmacological agent.

15. The method of claim 1, wherein the healthcare provider is a doctor, nurse, medical professional, or medical technician.

16. The method of claim 1, wherein the recurrent treatment includes an intraocular injection of a pharmacological agent.

17. The method of claim 1, wherein the one or more visual function tests are pre-selected by a healthcare provider based on analysis of the retinal imaging.

18. The method of claim 1, wherein the retinal disease is dry macular degeneration disease and the tests are pre-selected to determine progression to wet macular degeneration disease.

19. The method of claim 1, wherein the analysis of the results of the visual function evaluations includes comparing the results to an expected level of performance for the patient, determined from previous visual function evaluation results and sending an alert to the healthcare provider if the recent results of the visual function evaluation for the patient deviate from the expected level of performance by more than a specified delta level, wherein the delta level is specified by a medical professional.

20. The method of claim 1, wherein the retinal disease includes one or more conditions from the list: macular degeneration, diabetic retinopathy, diabetic macular edema, retinal vein occlusion, glaucoma, and chronic retinal detachment.

* * * * *